United States Patent
Kim et al.

(10) Patent No.: US 6,255,317 B1
(45) Date of Patent: *Jul. 3, 2001

(54) CHOLESTEROL BIOSYNTHESIS INHIBITORS

(75) Inventors: Jung Ho Kim, Daejeon; Tae Neung Jhong, Kyonggi-do; Young Ki Paik, Seoul; Joon Seo Park; Eui Deok Kim, both of Daejeon; You Suk Lee, Seoul; Seung Un Kim, Daejeon, all of (KR)

(73) Assignee: Hanwha Chemical Corporation (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/233,325

(22) Filed: Jan. 20, 1999

(30) Foreign Application Priority Data

Sep. 25, 1998 (KR) ................................... 98-40007

(51) Int. Cl.⁷ ..................... C07D 487/04; C07D 471/04; A61K 31/4375; A61K 31/4355
(52) U.S. Cl. .......................... 514/280; 514/282; 546/48; 546/71
(58) Field of Search ........................ 546/71, 48; 514/280, 514/282

(56) References Cited

U.S. PATENT DOCUMENTS

| | | | |
|---|---|---|---|
| 3,835,140 | 9/1974 | Zee-Cheng et al. | 546/71 |
| 4,033,966 | 7/1977 | Sawa | 546/71 |
| 4,042,592 | 8/1977 | Sawa | 546/71 |
| 4,087,426 | 5/1978 | Shamma et al. | 546/48 |
| 4,200,629 | 4/1980 | Nakamura | 424/195.1 |
| 4,761,417 | 8/1988 | Maroko | 514/284 |
| 4,761,477 | 8/1988 | Ikekawa et al. | 546/48 |
| 4,980,344 | 12/1990 | Maroko | 514/26 |
| 6,028,197 | * 2/2000 | Kim et al. | 546/48 |
| 6,030,979 | 2/2000 | Kim et al. | 514/280 |

FOREIGN PATENT DOCUMENTS

| | | |
|---|---|---|
| 2043218 | 9/1970 | (DE) . |
| 1265627 | 8/1970 | (GB) . |
| 64021530 | 1/1964 | (JP) . |

OTHER PUBLICATIONS

Fukuda et al., Chem. Pharm. Bull., vol. 18, No. 7, p. 1299–1304 (1970).
Naruto et al., Tetrahedron Lett., vol. 19, p. 1597–1600 (1976).
Karas–Gasparec et al., CA Accession No. 1968:46980 (1968).

* cited by examiner

Primary Examiner—Alan L. Rotman
(74) Attorney, Agent, or Firm—Hunton & Williams

(57) ABSTRACT

The present invention provides a cholesterol biosynthesis inhibitor which specifically inhibits the sterol 14-reductase which is involved in the distal pathway of cholesterol biosynthesis, a compound of formula (1) below and the use of an extract or the compound of formula (1) for treating hypercholesterolaemia or hyperlipidaemia. The inhibitor comprises an extract obtained by extracting *Corydalis Turtschaninowii Besser* with a solvent, or an organic layers obtained by partitioning an extract from *Corydalis Turtschaninowii Besser* with an organic solvent. The extract contains 7,8,13,13α-tetrahydrocoridaline or its derivative, as the active ingredients, which specifically inhibits the enzyme which is involved in the distal pathway of the cholesterol biosynthesis.

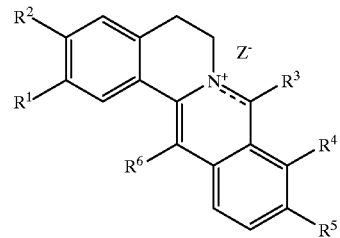

(1)

$R^1$ and $R^2$ which may be the same or different from each other, represent a hydroxy group or an alkoxy group having 1 to 4 carbon atoms or both of $R^1$ and $R^2$ represent a methylenedioxy group;

$R^3$ represents a hydrogen atom;

$R^4$ and $R^5$ which may be the same or different from each other, represent a hydroxy group, a hydroxyethylamino group or an alkoxy group having 1 to 4 carbon atoms;

$R^6$ represents a hydrogen atom, an alkyl group having 1 to 8 carbon atoms, an alkenyl group having 3 to 8 carbon atoms, a cycloalkylalkyl group having 1 to 7 carbon atoms, a holoalkyl group having 1 to 4 carbon atoms, an ethoxycarbonyl group, an ethoxycarbonylmethyl group, a hydroxycarbonylmethyl group, 1-ethoxycarbonylethyl group, or 2-valerolactonyl group; and z represents a halogen atom.

11 Claims, No Drawings

CHOLESTEROL BIOSYNTHESIS INHIBITORS

TECHNICAL FIELD

The present invention relates to a cholesterol biosynthesis inhibitor. More specifically, the present invention relates to a new class of inhibitor which specifically inhibits the sterol 14-reductase which is involved in the distal pathway of cholesterol biosynthesis. The inhibitor comprises an extract obtained by extracting *Corydalis Turtschaninowii Besser* with a solvent, or an organic layer obtained by partitioning an extract from *Corydalis Turtschaninowii Besser* with an organic solvent. The extract contains 7,8,13,13α-tetrahydrocoridaline or its derivatives, as a main igredient. The present invention also relates to a novel compound of formula (1) as set forth below and to the use of the extract or the compound of formula (1) for treating hypercholesterolemia or hyperlipidaemia.

BACKGROUND ART

Cholesterol is an important vital constituent of cell membrane in mammal and is involved in cell division, growth, development and control of differentiation, and also is a precursor of various essential metabolites (for example, steroid hormones, bile acids). However, it may cause hyperlipidaemia which leads to atherosclerosis if its intake or production within the body is excess. Hyperlipidaemia leads to cardiovascular disease which is a leading cause of death in humans. It is usually caused when cholesterol or triglyceride has exceeded a proper level (i.e., total cholesterol level for adults at the age of between 30 and 40 is about 200 mg/dl), and then, deposited to the inner wall of an artery to form atheroma plaques, thereby blood flow being inhibited which causes cardiac failure or cerebral stroke. Cholesterol is synthesized mainly in the liver in mammals and the synthetic pathway thereof is started from acetyl-CoA and is completed after at least 32 steps of enzyme reactions.

Cholesterol biosynthesis which occurs in mammal can be summarized according to the enzyme reaction patterns in which each intermediate is formed as in the following reaction scheme 1.

Reaction Scheme 1

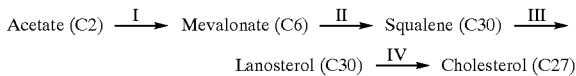

In the above reaction scheme, steps I and II undergo polymerization, and steps II and III undergo cyclization. In step IV, transformation, demethylation, isomerization or reduction of steroid ring is proceeded. Cholesterol biosynthesis is carefully controlled by the multi-step regulation, i.e., the so-called multivalent coordinate regulation. For example, 3-β-hydroxymethylglutaryl-CoA reductase (HMG-CoA reductase) is the main rate-limiting enzyme in the cholesterol biosynthesis. It reduces HMG-CoA synthesized from acetyl-CoA during the early stage of the biosynthetic pathway starting from acetate (C2) to mevalonate (C6) and is inhibited in vivo by the fimal product, cholesterol. More specifically, the activity of this enzyme is controlled by dietary cholesterol, oxysteroids and mevalonate derivatives in a feed-back inhibition manner. For the past decade, the lipid-lowering agents have been developed based on their inhibiting activities against this enzyme. Most of currently marketed therapeutic agents for hyperlipidaemia which have been developed based on such mechanism include, for example, statins including lovastatin, pravastatin, simvastatin, atorvastatin, and cerivastatin. However, if cholesterol biosynthesis is suppressed by inhibiting the activity of HMG-CoA reductase which is the rate liniting enzyme at the early stage of cholesterol biosynthesis, there may be many side effects that the synthesis of many important biomolecules such as dolicol, isopentenyl pyrophosphate, haem A, and ubiquinone which are also derived from mevalonate are suppressed together.

Therefore, it may be advantageous to block cholesterol biosynthesis at a step distal to HMG CoA reductase in order to prevent depletion of such essential intermediates.

Accordingly, recent researches have been focused on the development of new type of therapeutic agents for hyperlipidaemia which can effectively block only the post-squalene steps without interfering HMG-CoA reductase activity. For example, the activation mechanisms of the distal enzymes responsible for the postsqualene pathway in the cholesterol biosynthesis which comprises the sequence of 'squalene→lanosterol→zymosterol→desmosterol→cholesterol' have been studied and attempts to screen and develop a drug which can specifically inhibit the activity of the target enzyme responsible for the distal pathway of cholesterol biosynthesis based have been made. Especially, based on the inhibitory activity of squalene epoxidase responsible for the pathway of 'squalene→lanosterol', a benzylamine series compound, NB598 has been developed by Banyu Pharmaceutical Co. of Japan; Squalenestatin I has been developed by the researchers of Glaxo Wellcome Limited, a British company on the basis of its inhibition of squalene synthase which is responsible for the synthesis of squalene from farnesyl pyrophosphate.

RPR107393 has been developed as a potent squalene synthase inhibitor by researchers at Rhone-Poulenc, France. Further, Taton et al. have reported MDL 28,815 having 8-azadecaline ring based on the inhibition of 2,3-oxidosqualene cyclase responsible for the cyclization reaction in which squalene epoxide is converted into methylsterol (See, Biochem. Biophys. Res. Commun. 1986, 138, 764–70). These NB598, Squalenestatin I, RPR107393 and MDL 28,815 which inhibit the activities of enzymes responsible for the post-mevalonate pathway in the cholesterol biosynthetic pathway have a merit that they can selectively inhibit the cholesterol biosynthesis without effecting on the production of other important intermediates which are derived from mevalonate, differently from drugs that have a target on HMG-CoA reductase responsible for the early stage of cholesterol biosynthesis.

However, these agents are not yet currently marketed as therapeutic agents for hyperlipidaemia.

DISCLOSURE OF THE INVENTION

The present inventors have conducted an extensive research for many years in order to develop a novel class of cholesterol biosynthetic inhibitor which specifically inhibits the enzyme involved in the steps of 'lanosterol→cholesterol'. As a result, the inventors have surprisingly discovered that an extract obtained from *Corydalis Turtschaninowii Besser* which has been used in the prescription of sedative agent or hemostatic agent in the oriental medicine for thousand years strongly inhibits the activity of sterol 14-reductase which catalyzes the reduction of 4,4-dimethyl-8,14-dien-3β-ol and thus have completed the present invention.

Based on these findings, it is possible to provide a cholesterol biosynthesis inhibitor which comprises an extract obtained from *Corydalis Turtschaninowii Besser* containing 7,8,13,13α-tetrahydrocoridaline as the main component which specifically inhibits the sterol 14-reductase in the distal pathway of the cholesterol biosynthesis.

It is therefore an object of the present invention to provide a cholesterol biosynthesis inhibitor which comprises an extract obtained by extracting *Corydalis Turtschaninowii Besser* with one or more solvent selected from the group consisting of water, alcohols, such as methanol, ethanol, and dichloromethane and/or an organic fraction obtained by partitioning an extract from *Corydalis Turtschaninowii Besser* with an organic solvent such as dichloromethane.

Another object of the present invention is to provide a cholesterol biosynthesis inhibitor which comprises the components isolated from the organic fraction of the above *Corydalis Turtschaninowii Besser* extract or synthetic derivatives of the components.

A further object of the present invention is to provide protoberberine(5,6-dihydrodibenzo-[a,g]quinolizinium) derivatives or 13,13α-didehydroberbine derivatives or the salts thereof which can be represented by formula (1) as set forth below.

Still another object of the present invention is to provide a composition for inhibiting cholesterol biosynthesis, especially inhibiting sterol 14-reductase, which comprises 7,8,13,13α-tetrahydrocoridaline, or protoberberine (5,6-dihydrodibenzo-[a,g]quinolizinium) derivatives, 13,13α-didehydroberbine derivatives or the salts thereof which can be represented by formula (1) below and a pharmaceutically acceptable carrier.

A still further object of the present invention is to provide a pharmaceutical composition for treating hypercholesterolemia or hyperlipidaemia which comprises pharmaceutically effective amount of the above extract, the organic fraction or the synthetic derivatives as an active ingredient and a pharmaceutically acceptable carrier.

Still another object of the present invention is to provide a method for treating hypercholesterolemia and hyperlipidaemia by inhibiting cholesterol biosynthesis, especially inhibiting sterol 14-reductase with the above pharmaceutical composition.

Further objects and advantages of the invention will become apparent through reading the remainder of the specification.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the detailed description of the preferred embodiment in addition to the scope of the invention defmed by the Claims.

Hereinbelow, the application will be illustrated in more detail.

The extract from *Corydalis Turtschaninowii Besser* according to the present invention can be prepared by triturating *Corydalis Turtschaninowii Besser* into small pieces, extracting them with a 80% ethanol in warm bath, filtering the extract, and evaporating the extracted solution under reduced pressure to remove the solvent. As the solvent for the extraction, water, alcohols such as methanol or ethanol, dichloromethane or the mixture thereof may be preferably used.

*Corydalis Turtschaninowii Besser* is an annual plant widely distributed in the mountains and fields of Korea and has been used in the prescription of sedative agent or hemostatic agent in the oriental medicine. An extract of *Corydalis Turtschaninowii Besser* contains a lot of alkaloids as a major active component, of which is coridaline in the form of quaternary ammonium salt. This coridaline in the form of quatenary ammonium salt has been known to have a week sedative action and a strong gastric juice secretion action, and UK Patent No. 1,265,627 and German Patent No. 2,043,218 disclose its use as an anti-ulcer agent.

However, the use of an extract obtained from *Corydalis Turtschaninowii Besser* comprising 7,8,13,13α-tetrahydrocoridaline, an alkaloid, the main component of which is coridaline as a cholesterol biosynthesis inhibitor has not yet been reported. The inventors of the present invention have discovered the use of *Corydalis Turtschaninowii Besser* as a cholesterol synthesis inhibitor in the course of screening new cholesterol biosynthesis inhibitor based on the oriental medicine. This discovery was fully supported by the method using a screening an activity of sterol 14-reductase that was established by the inventors since the inventors have started the research for a new drug.

The detailed screening method will be explained in detail in the working examples. Thus, the principle thereof will be briefly explained hereinbelow.

That is, sterol 14-reductase is one of the main regulatory enzymes for lanosterol→cholesterol pathway and is responsible for the reduction of the double bond formed when methyl group attached to the carbon at 14-position of lanosterol is demethylated. First, a screening system for sterol 14-reductase was constructed in which 4,4-dimethyl-5α-cholesta-7,14-dien-3β-ol is used as a substrate and then, the effect on the activity of sterol 14-reductase was investigated in the screening system. It is possible to obtain the correlation that a substance inhibiting the activity of sterol 14-reductase inhibits cholesterol biosynthesis by comparing the results obtained from the screening tests with those of the actual animal experiments.

The synthetic derivative for the purpose of the present invention is rotoberberine (5,6-dihydro-dibenzo-[a,g]quinolizinium) or 13,13α-didehydroberbine derivative which can be represented by the formula (1) below.

(1)

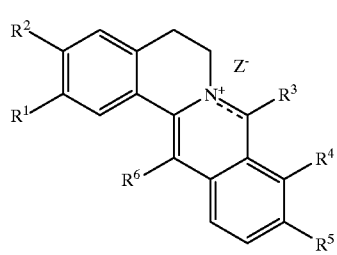

wherein, if

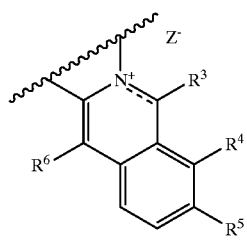 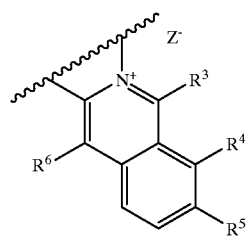 is $R^1$ and $R^2$ which may be the same or different from each other, represent a hydroxy group or an alkoxy group having 1 to 4 carbon atoms or both of $R^1$ and $R^2$ represent a methylenedioxy group;

$R^3$ represents a hydrogen atom;

$R^4$ and $R^5$ which may be the same or different from each other, represent a hydroxy group, a hydroxyethylamino group or an alkoxy group having 1 to 4 carbon atoms;

$R^6$ represents a hydrogen atom, an alkyl group having 1 to 8 carbon atoms, an alkenyl group having 3 to 8 carbon atoms, a cycloalkylalkyl group having 1 to 7 carbon atoms, a holoalkyl group having 1 to 4 carbon atoms, an ethoxycarbonyl group, an ethoxycarbonylmethyl group, a hydroxycarbonylmethyl group, 1-ethoxycarbonylethyl group, or 2-valerolactonyl group; and Z represents a halogen atom, or wherein, if

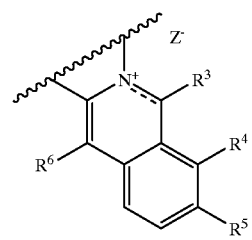 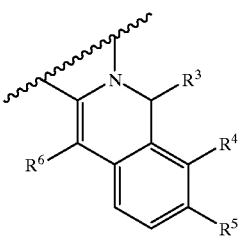 is $R^1$ and $R^2$ which may be the same or different from each other, represent a hydroxy group or an alkoxy group having 1 to 4 carbon atoms or both of $R^1$ and $R^2$ represent a methylenedioxy group;

$R^3$ represents a hydrogen atom; an alkyl group having 1 to 8 carbon atoms, a ketonyl group having 3 to 7 carbon atoms, a cycloalkyl group having 3 to 7 carbon atoms, a cyanomethyl group, 2-cyclopentanonyl group, or 2-cyclohexanonyl group;

$R^4$ and $R^5$ which may be the same or different from each other, represent a hydroxy group, a hydroxyethylamino group or an alkoxy group having 1 to 4 carbon atoms;

$R^6$ represents a hydrogen atom, an alkyl group having 1 to 8 carbon atoms, an alkenyl group having 3 to 8 carbon atoms, or a cycloalkylalkyl group having 1 to 7 carbon atoms.

The cholesterol biosynthesis inhibitor according to the present invention, especially protoberberine(5,6-dihydrodibenzo-[a,g]quinolizinium) derivative, 13,13α-didehydroberbine derivative or the salts thereof as the inhibitor of sterol 14-reductase can preferably be represented by Tables 1 and 2 below:

TABLE 1 formula (1a)

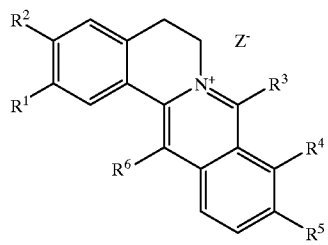

protoberberine derivative

| Compound No. | $R^1$ | $R^2$ | $R^4$ | $R^5$ | $R^6$ | Z | m.p. (° C.) |
|---|---|---|---|---|---|---|---|
| 1 | —O—CH$_2$—O— | | CH$_3$O | CH$_3$O | CH$_3$ | I | 168 |
| 2 | OH | OH | CH$_3$O | CH$_3$O | CH$_3$ | Cl | 145 |
| 3 | OH | OH | OH | OH | H | Cl | 163 |
| 4 | OH | OH | OH | OH | CH$_3$ | Cl | 255 |
| 5 | EtO | EtO | EtO | EtO | Et | Cl | 128 |
| 6 | —O—CH$_2$—O— | | CH$_3$O | CH$_3$O | Et | I | 230 |
| 7 | OH | OH | OH | OH | Et | Cl | 280 |
| 8 | CH$_3$O | CH$_3$O | CH$_3$O | CH$_3$O | Et | Cl | 186 |
| 9 | —O—CH$_2$—O— | | CH$_3$O | CH$_3$O | Allyl | I | 165 |
| 10 | OH | OH | OH | OH | Allyl | Cl | 234 |
| 11 | CH$_3$O | CH$_3$O | CH$_3$O | CH$_3$O | n-Pr | I | 190 |
| 12 | CH$_3$O | CH$_3$O | CH$_3$O | CH$_3$O | n-Bu | I | 170 |
| 13 | CH$_3$O | CH$_3$O | CH$_3$O | CH$_3$O | 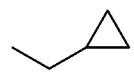 | I | 230 |

TABLE 1-continued
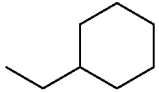
formula (1a)
protoberberine derivative
| Compound No. | R¹ | R² | R⁴ | R⁵ | R⁶ | Z | m.p. (° C.) |
|---|---|---|---|---|---|---|---|
| 14 | CH₃O | CH₃O | CH₃O | CH₃O | n-Octyl | I | 128 |
| 15 | CH₃O | CH₃O | CH₃O | CH₃O | 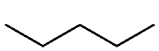 | I | 198 |
| 16 | CH₃O | CH₃O | CH₃O | CH₃O | 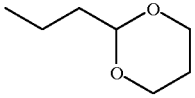 | I | 156 |
| 17 | n-BuO | n-BuO | n-BuO | n-BuO | H | Cl | 180 |
| 18 | CH₃O | CH₃O | CH₃O | CH₃O |  | Cl | 146 |
| 19 | CH₃O | CH₃O | CH₃O | CH₃O | 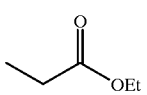 | Cl | 92 |
| 20 | CH₃O | CH₃O | CH₃O | CH₃O | 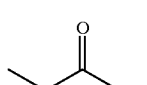 | Cl | 200 |
| 21 | CH₃O | CH₃O | CH₃O | CH₃O | 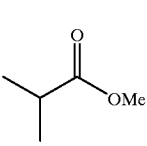 | Cl | 198 |
| 22 | —O—CH₂—O— | | CH₃O | CH₃O | 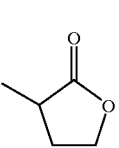 | Br | 187 |
| 23 | —O—CH₂—O— | | CH₃O | CH₃O | 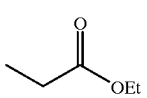 | Br | 240 |
| 24 | —O—CH₂—O— | | CH₃O | CH₃O | 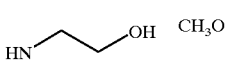 | Br | 165 |
| 25 | CH₃O | CH₃O | HN⁀⁀OH | CH₃O | Et | Cl | 214 |

TABLE 2

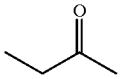

formula (1b)

13,13α-didehydroberbine derivative

| Compound No. | R¹ | R² | R⁴ | R⁵ | R³ | R⁶ | m.p. (° C.) |
|---|---|---|---|---|---|---|---|
| 26 | —O—CH₂—O— | | CH₃O | CH₃O | —CH₂—C(=O)—CH₂CH₃ | H | 130 |
| 27 | —O—CH₂—O— | | CH₃O | CH₃O | CH₃ | H | 96 |
| 28 | —O—CH₂—O— | | CH₃O | CH₃O | Et | H | 90 |
| 29 | —O—CH₂—O— | | CH₃O | CH₃O | n-Pr | H | 90 |
| 30 | —O—CH₂—O— | | CH₃O | CH₃O | n-Bu | H | 68 |
| 31 | —O—CH₂—O— | | CH₃O | CH₃O | —CH₂—cyclohexyl | H | 107 |
| 32 | —O—CH₂—O— | | CH₃O | CH₃O | i-Pr | H | 98 |
| 33 | CH₃O | CH₃O | CH₃O | CH₃O | CH₃ | H | 75 |
| 34 | CH₃O | CH₃O | CH₃O | CH₃O | Et | H | 86 |
| 35 | —O—CH₂—O— | | CH₃O | CH₃O | n-Octyl | H | liquid |
| 36 | —O—CH₂—O— | | CH₃O | CH₃O | —CH₂—cyclopropyl | H | 162 |
| 37 | CH₃O | CH₃O | CH₃O | CH₃O | —CH₂—C(=O)—CH₂CH₃ | Et | 156 |
| 38 | CH₃O | CH₃O | CH₃O | CH₃O | —CH₂CH₂—C(=O)—CH₂CH₃ | Et | 127 |
| 39 | CH₃O | CH₃O | CH₃O | CH₃O | —CH₂—C(=O)—CH(CH₃)₂ | Et | 72 |
| 40 | CH₃O | CH₃O | CH₃O | CH₃O | —CH₂CH₂—C(=O)—CH₂CH(CH₃)₂ | Et | 127 |
| 41 | CH₃O | CH₃O | CH₃O | CH₃O | —CH₂CH₂—CN | Et | 147 |
| 42 | CH₃O | CH₃O | CH₃O | CH₃O | —CH₂—(2-methylcyclopentan-1-onyl) | Et | 165 |

TABLE 2-continued formula (1b)

[structure of 13,13α-didehydroberbine derivative]

13,13α-didehydroberbine derivative

| Compound No. | R¹ | R² | R⁴ | R⁵ | R³ | R⁶ | m.p. (° C.) |
|---|---|---|---|---|---|---|---|
| 43 | CH₃O | CH₃O | CH₃O | CH₃O | [2-methylcyclohexanone] | Et | 125 |
| 44 | EtO | EtO | EtO | EtO | [butan-2-one] | Et | 108 |
| 45 | EtO | EtO | EtO | EtO | [2-methylpentan-3-one] | Et | 103 |
| 46 | CH₃O | CH₃O | CH₃O | CH₃O | H | Et | 122 |
| 47 | EtO | EtO | EtO | EtO | H | Et | 103 |
| 48 | CH₃O | CH₃O | CH₃O | CH₃O | CH₃ | Et | 134 |
| 49 | CH₃O | CH₃O | CH₃O | CH₃O | Et | Et | 153 |
| 50 | CH₃O | CH₃O | CH₃O | CH₃O | n-Bu | Et | 112 |

A part of the compounds represented by the formula (1) according to the present invention may exist as the main component for *Corydalis Turtschaninowii Besser* alkaloid. However, since the amount thereof available from nature is limited, it may be synthesized starting from the compound of formula (4) below according to the reaction scheme 2 below as described in UK Patent No. 1,265,627.

Reaction Scheme 2

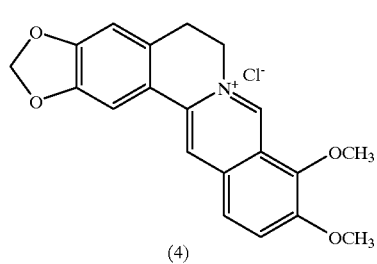

(4) Step 1

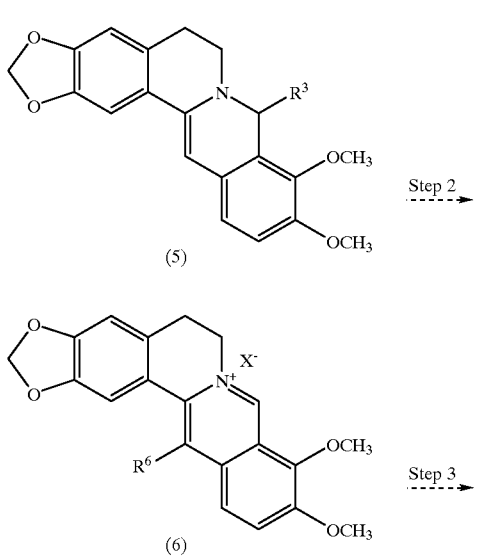

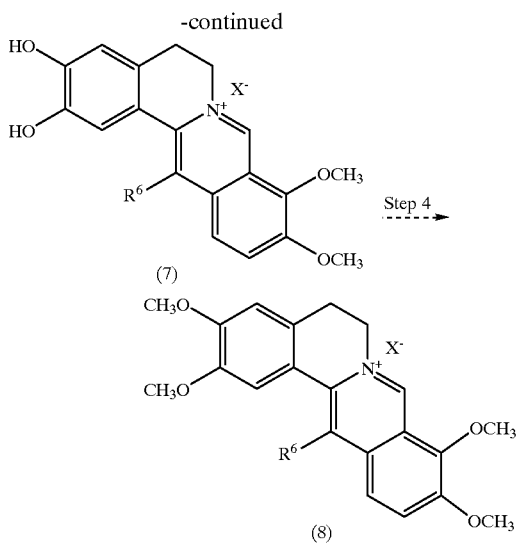

In the above reaction scheme 2, $R^3$ and $R^6$ are the same as defined in the above compound of formula (1), and $X^-$ represents a halide, a sulfate, or a nitrate.

In the first step of the reaction scheme, berberine salt of structural formula (4) is reacted with a ketone compound under the presence of a base such as sodium hydroxide or diisopropyl amine and normal butyl lithium to give 8-ketonylberberine compound represented by formula (5) or reacted with alkyl lithium or akyl magnesium halide to give 8-alkyl berberine compound represented by formula (5).

In the second step, 8-acetonylberberine and alkyl halide are reacted at 50~100° C. in a polar solvent such as acetonitrile or a non-polar solvent such as toluene to give 13-alkylberberine halide of formula (6).

The third step of the above reaction scheme involves the cleavage reaction of 2,3-methylenedioxy ring in which the compound of formula (6) is reacted with Lewis acid such as anhydrous aluminum chloride at 80~160° C. and then subjected to hydrolysis reaction with a dilute acid. According to the reaction conditions, 13-alkyl-2,3-dihydroxy compound may be produced as a major product along with 2,3,9-trihydroxy-, or 2,3,9,10-tetrahydroxy compound and these compounds can be separated by recrystalization method. However, it may be possible to be used in the fourth step reaction without further separation process.

The fourth step involves a reaction in which the compound of formula (7) obtained from the previous step is methylated with a methylating reagent such as dimethyl sulfate or iodomethane to give 13-alkylpalmatine salt of formula (8). In this reaction step, the compound wherein alkyl at 13-alkyl group is methyl is dehydrocoridaline compound (comp. no. 8 in Table 1).

13-alkylpalmatine salt represented by formula (8) may be transformed into various salts such as halide, sulfate, nitrate, acetate, cinnamate, tinate, maleate, succinate, citrate, fumarate or fatty acid salt, etc. on the basis of the salts used in the purification process of the fourth step. The carbonyl group of ketone in the 8-ketonylberberine of formula (5) can be reduced using lithium aluminum hydride. Quaternary ammonium salts represented by the formulae (4), (6), (7) and (8) may be reduced with sodium borohydride ($NaBH_4$) in the presence of potassium carbonate to give tertiary amine compounds.

Meanwhile, among the protoberberine compound of formula (1a), the compound wherein $R^1$, $R^2$, $R^3$, $R^4$, $R^5$ and $R^6$ each represents a methoxy group, a methoxy group, a hydrogen atom, a methoxy group, a methoxy group and an ethyl group and Z represents chloride, and the compound wherein $R^1$, $R^2$, $R^3$, $R^4$, $R^5$ and $R^6$ each represents an ethoxy group, an ethoxy group, a hydrogen atom, an ethoxy group, an ethoxy group and an ethyl group and Z represents chloride; and among the didehydroberbine compound of formula (1b), the compound wherein $R^1$, $R^2$, $R^3$, $R^4$, $R^5$ and $R^6$ each represents a methoxy group, a methoxy group, a 2-oxopropyl group, a methoxy group, a methoxy group and an ethyl group, and the compound wherein $R^1$, $R^2$, $R^3$, $R^4$, $R^5$ and $R^6$ each represents a methoxy group, a methoxy group, a hydrogen atom, a methoxy group, a methoxy group and an ethyl group and Z represents chloride are preferred in an aspect of the pharmaceutical efficacy.

The compound of formula (1) markedly inhibited the cholesterol biosynthesis in the cultured human liver cell culture (HepG2 cell line). In order to investigate the effect of the compound of formula (1) of the invention, the compound was orally administered into male Syrian Golden Hamsters having weights of 90~110 g and then blood was taken from each animal. Plasma lipids, i.e., total cholesterol, LDL-cholesterol, HDL-cholesterol and triglycerides were analyzed using an automatic analyzer (Automatic analyzer model Hitachi 7150). As the results, total cholesterol, LDL-cholesterol, and triglyceride levels were significantly decreased while HDL-cholesterol value was not significantly changed. In addition, the compound resulted in decrease in a certain degree in the glucose value within the serum.

The compound of formula (1) may be formulated into a pharmaceutical composition with pharmaceutically acceptable excipients or carriers. Especially, the composition can be desirably used as the therapeutic agents for treating hypercholesterolemia and hyperlipidaemia by inhibiting sterol 14-reductase. The composition may be formulated into a tablet, a syrup or an injection formulation and thus, can be administered orally. An effective dose will vary depending upon the kind of the excipients or carriers within the range for treating hypercholesterolemia and hyperlipidaemia with a dose of 0.3~60 mg/kg/day of active ingredient being preferable in case of oral administration.

BEST MODE FOR CARRYING OUT THE INVENTION

The present invention will be described in greater detail by way of the following examples and synthetic examples. The examples are provided for the purpose of illustration only and should not be construed as limiting the invention which is properly delineated in the Claims.

EXAMPLE 1

Inhibiting Effect of an Extract from *Corydalis Turtschaninowii Besser* on Sterol 14-Reductase in Microsome State 100 G of *Corydalis Turtschaninowii Besser* were homogenated and then, added into a 1L flask equipped with a reflux condenser together with 300 ml of 80% methanol. The mixture was extracted for 3 hours under reflux. The filtrates were combined and dried over a reduced pressure roller condenser at a temperature below 60° C. to give 9.2 g of *Corydalis Turtschaninowii Besser* extract. Separately, 20 male Sprague-Dawley rats weighing from 150 to 200 g have been fed a diet containing 0.1% (w/w) Lovastatin and 5% (w/w) Cholestyramine. The animals were fasted for 12 hours before excising liver tissues and then sacrificed by decapitation at midnight. An aqueous solution containing 0.25M of sucrose was injected into the hepatic portal vein to remove all the blood within the liver, and then, the liver was excised. The liver was homogenated with two volummes of buffer solution 1 (0.1 M potassium phosphate , 1 mM reduced glutathione, 0.5 mM EDTA, 20% (v/v) glycerol, pH 7.4) by repeating pestles over 10 times and then, centrifuged with 900×g for 5 minutes to give a supernatant. The supernatant was centrifuged with 12,000×g for 20 minutes. The supernatant obtained was ultracentrifuged with 105,000×g for 90 minutes to give a microsome which was used as an enzyme source of sterol 14-reductase. Assay against sterol 14-reductase was carried out as follows: 60 nmol of 4,4-dimethyl-5α-cholesta-7,14-dien-3β-ol and the extract from *Corydalis Turtschaninowii Besser* dissolved into DMSO were added to an assay mixture (total volume 1.0 ml) containing 2 mg of microsomal protein, 2 mM of NADPH and 25 mg of glucose plus 20 units of glucose oxidase with preincubations under nitrogen at 37° C. for 4 min unless otherwise specified to establish anaerobic condition. Buffer A (0.1M potassium phosphate buffer, pH 7.4, including 1 mM reduced glutathione, 0.5 mM EDTA, and 20% (v/v) glycerol) used for incubation had been equilibrated with nitrogen, and nitrogen was exchanged for air in all sealed reaction flasks prior to the start of incubations. Incubation of the complete mixture was carried out anaerobically in sealed flasks for 10 min at 37° C. unless otherwise indicated. Incubations were terminated by the addition of 1 ml of ethanolic KOH followed by heating under reflux for 10 min. Sterols were extracted four times with 4 ml of petroleum ether, and the solvent was evaporated to dryness under a nitrogen stream. The resulting residue was dissolved in 200–500 µl of n-hexane for quantification by GLC at high sensitive attenuation. The activity of sterol 14-reductase was determined with the amount of the substrate wherein the double bonds of 14-carbon were reduced (for the amount reduced by 1 mg of the microsome protein for 1 minute). When *Corydalis Turtschaninowii Besser* level added to the reaction system was 5 mg/ml, 57% of inhibition of the enzymatic activity was observed.

EXAMPLE 2

Effect of Alkaloid Fractions from *Corydalis Turtschaninowii Besser* on Sterol 14-Reductase Activity 10.0 G of *Corydalis Turtschaninowii Besser* extracts were dissolved into 200 ml of distilled water and the mixture was then transferred to a separatory funnel. Solvent partition was carried out with 200 ml of dichloromethane. After layers were separated, dichloromethane layers were combined together and this extraction procedure was repeated twice with 150 ml of dichloromethane. Combined organic extracts were dried over anhydrous magnesium sulfate, filtered and concentrated. After removing solvent with a vacuum pump, 1.45 g of the organic fractions in powder were obtained. The organic solvent fractions of *Corydalis Turtschaninowii Besser* extracts obtained by the above procedure were dissolved in DMSO and tested for the activity on sterol 14-reductase as the same manner in Example 1. When the fraction level was 50 µg/ml, 37% of inhibitory effect was observed.

EXAMPLE 3

Effect of the Alkaloid Fractions from *Corydalis Turtschaninowii Besser* on Cholesterol Biosynthesis Ratio in CHO Cells Chinese hamster ovary cell (CHO cell) was passage-cultivated on the flat plates. When colonies reached at 70 to 80% of area based on the total culture area, culture medium was replaced with a fresh medium and this was then used as samples for determining sterol 14-reductase activity and the cholesterol biosynthesis ratio.

Cholesterol biosynthesis ratio was determined by the Boogaard method [See, Biochem. J. 1987, 241, 345–51] with some modification. To the three dishes (diameter: 60 nm) containing the above CHO cells, the extracts obtained from Example 2 were added and the mixture was then incubated for 30 minutes. After adding each 0.5 µCi of $^{14}$C-Mevalonate into the medium, incubation was continued for 2 hours. Culture medium was removed from the vessel, and the mixture was then washed 3 times with PBS at 4° C. The cells were scratched and collected in about 1.0 ml of PBS, and then subjected to centrifugation at 10,000 rpm for 5 min. In order to determine cholesterol having radioactivity, the cell precipitates were first floated with 0.1N NaOH. After quantifying proteins in the floats, the floated material were taken so as to contain a suitable amount of proteins. The total volume was adjusted to 1.0 ml with the buffer solution 1 and added 1.0 ml of 25% ethanolic KOH solution thereto to proceed saponification reaction at 80° C. for 30 minutes. After dissolving unsaponicated sterols into n-hexane, they were separated by a thin layer liquid chromatography. The composition of the developing solvents was ethyl acetate and benzene at 95:5 ratio and cholesterol was developed as the internal standard for 50 minutes. Bands in the cholesterol-developed peak region were collected and put into a radioactive vial, and then 10 ml of scintillation cocktail solution were added thereto. The radioactivity strength of each sample was determined by a liquid scintillation counter (LSC) to give the cholesterol biosynthetic ratio. 81% of inhibitory effect was observed at the 50 µg/ml concentration of the organic fractions from the extract.

EXAMPLE 4

Effect of 7,8,13,13α-Tetrahydrocoridaline which is an Active Ingredient of *Corydalis Turtschaninowii Besser* on Sterol 14-Reductase Activity 3.0 G of the organic fraction powder were adsorbed on celite and it was then placed on the upper end of the liquid chromatography for aliquot. Dichloromethane and ethanol were used as elution solvents. At the early pathway of the chromatography, elution was carried out with dichloromethane only, and then, ethanol content was gradually increased. It was confirmed by the thin layer chromatography that most of 7,8,13,13α-tetrahydrocoridaline with a small amount of impurity were found in the fractions in which 4~6% of ethano/dichloromethane elution solvent were used. The fractions were combined, concentrated and then refluxed in distilled water for 10 minutes. Undissolved components were filtered off and the filtrate was stored for 24 hours in a refrigerator. The crude crystals formed were dried and then recrystallized from methanol to give 120 mg of 7,8,13,13α-tetrahydrocoridaline. The structure of 7,8,13,13α-tetrahydrocoridaline was identified with the nuclear magnetic resonance spectrometer, mass analyzer, and infrared spectrometer. The result are set forth below.

$^1$H-NMR (CD$_3$OD, 300 MHz), δ: 3.00(s, 3H), 3.21(t, 2H), 3.95(s, 3H), 4.01(s, 3H), 4.11(s, 3H), 4.24(s, 3H), 4.25(s, 3H), 7.93(t, 2H), 6.96(s, 1H), 7.20(s, 1H), 7.91(d, 1H), 9.94(s, 1H); $^{13}$C-NMR (CD$_3$OD,75 MHz), δ: 18.66, 28.51, 56.72, 56.99, 57.44,58.12,62.74, 111.29, 114.46, 120.84, 120.95, 121.93, 126.45, 130.12, 132.36, 134.23, 137.05, 144.50, 145.51, 148.31, 150.77, 151.80; Positive FAB MIS: m/e 366(Base peak); IR(KBr) cm$^{-1}$: 3410, 1381, 1254, 1112, 1020.

7,8,13,13α-tetrahydrocoridaline obtained from the above procedure was dissolved in DMSO and was determined for its activity on sterol 14-reductase. As the result, 50/o of inhibitory effect was observed when the assay contained 40~50 μmol/ml of the active ingredient.

EXAMPLE 5

Effect of Dehydrocoridaline Derivatives on Sterol 14-Reductase Activity

Ethylpalmatine (compound no. 8) prepared in Synthetic Example 8 below was determined for its inhibitory activity against sterol 14-reductase as the same manner in Example 4. As a result, 50% of inhibitory effect were observed when the assay contained 0.1~3 μmol/ml of the active ingredient.

EXAMPLE 6

Effect of Dehydrocoridaline Derivatives on Cholesterol Biosynthesis in Cultured Human Liver Cell Line (HepG2 cells)

Cultured human liver HepG2 cell line was grown on RPMI (Rosewell park Memorial Institute) 1640 culture medium containing 10% PBS until 60% of monolayer are formed in a 60 mm culture dish. After replacing the medium with 3 ml of a fresh culture medium containing 10%(v/v) LPDS (Fetal calf lipoprotein-deficient serum), the cells were further grown for 48 hours until 90% of cultivation degree appear. The culture medium was removed and the cell was then washed with PBS. 2 ml of culture medium containing compound no. 8 (final concentration 100 μM) and AY-9944 (final concentration 1 μM) were added thereto. Then, the medium was cultivated at 37° C. for 1 hour under the condition of 95% air/5% carbonic acid gas. AY-9944 which is an inhibitor for sterol 7-reductase was used as a control drug for assuring the present experimental procedure on the inhibition of cholesterol biosynthesis. Thereafter, 3 μCi of [1,2-$^{14}$C]acetate (72 mCi/mmol) were added thereto. The cultivation was continued for 2 hours so that the isotope is introduced into the cell and used as a precursor for sterol to be synthesized. Then, the culture medium was completely removed and washed with PBS twice and the cells were collected by scratching. 10 μg of cholesterol, 10 μg of lanosterol and [$^3$H]cholesterol (30,000 dpm) were added thereto, and saponification reaction was carried out at 70° C. for an hour by adding 7.5% of methanolic KOH solution. Unsaponified sterol was removed by extracting them three times with 3 ml of petroleum ether and dried with nitrogen purging. The dried samples were redissolved in 200 μl of chloroform. An aliquot of the samples was loaded onto Silicagel 60F thin layer plate and then separated using ethyl acetate/hexane 25/75 (v/v) as the developing solvent. The thin layer film was developed by exposure to Amersham Hyperfilm at –70° C. for 7 days. Cholesterol band were confirmed by comparing the band appeared in the film and that appeared in the iodine-stained thin layer. After scratching the cholesterol band, it was quantified by a liquid scintillation counter.

EXAMPLE 7

In Vivo Effect of Dehydrocoridaline Derivatives on Cholesterol Biosynthesis in Syrian Golden Hamster Male Syrian Golden Hamsters weighing 90~110 g distributed from Samyuk Animal Laboratory, Seoul, Korea were bred under the following conditions: They were maintained under reverse light cycle (light cycle: from 6 P.M to 6 A.M; dark cycle: from 6 A.M. to 6 P.M.). The food and water were supplied at 10 A.M. The commercially available standard rodent chows were used. The hamsters were divided into 6 or 7 animals per group. The animals were fasted for 12 hours before administrating the drug. Then, dehydrocoridaline derivatives dissolved in a 0.25% methyl cellulose solution was administered orally for 14 days at the indicated time per a day. After fasting animals for 24 hours from the last administration, blood was extracted using a cardiac puncture and plasma was then isolated. Plasma lipids, i.e., total cholesterol, LDL-cholesterol, HDL-cholesterol and triglyceride values were analyzed using Automatic Analyzer (Hitachi 7150).

EXAMPLE 8

Preparation of Pharmaceutically Available Tablets of Dehydrocoridaline Derivatives The raw drug materials corresponding to an amount of 10,000 tablets were weighted and passed into 20 mesh sieve and the mixture was then blended for 10 minutes. The mixture was transferred to a compressor and was tableted under suitable pressure so as to give average weight of 200 mg per tablet.

1) Composition of the raw drug materials per tablet (200 mg)

| Component | amount |
|---|---|
| Compound No. 8 | 10 mg |
| Calcium carboxymethyl cellulose | 5 mg |
| Lactose #100 (100 mesh) | 147.5 mg |
| Hydroxypropyl cellulose | 5 mg |
| Ludipress (BASF AG) | 30 mg |
| Magnesium stearate | 2.5 mg |

2) Composition of the raw drug materials per tablet (200 mg)

| Component | amount |
|---|---|
| Compound No. 8 | 10 mg |
| Calcium carboxymethyl cellulose | 5 mg |
| Lactose #100 (100 mesh) | 147.5 mg |
| Hydroxypropyl cellulose | 5 mg |
| Kollidon VA64 (BASF AG) | 30 mg |
| Magnesium stearate | 2.5 mg |

3) Composition of the raw drug materials per tablet (200 mg)

| Component | amount |
|---|---|
| Compound No. 37 | 5 mg |
| Calcium carboxymethyl cellulose | 5 mg |
| Lactose #100 (100 mesh) | 152.5 mg |
| Hydroxypropyl cellulose | 5 mg |
| Ludipress (BASF AG) | 30 mg |
| Magnesium stearate | 2.5 mg |

4) Composition of the raw drug materials per tablet (200 mg)

| Component | amount |
|---|---|
| Compound No. 37 | 5 mg |
| Calcium carboxymethyl cellulose | 5 mg |
| Lactose #100 (100 mesh) | 152.5 mg |
| Hydroxypropyl cellulose | 5 mg |
| Kollidon VA64 (BASF AG) | 30 mg |
| Magnesium stearate | 2.5 mg |

5) Composition of the raw drug materials per tablet (200 mg)

| Component | amount |
|---|---|
| Compound No. 46 | 2 mg |
| Calcium carboxymethyl cellulose | 5 mg |
| Lactose #100 (100 mesh) | 155.5 mg |
| Hydroxypropyl cellulose | 5 mg |
| Ludipress (BASF AG) | 30 mg |
| Magnesium stearate | 2.5 mg |

6) Composition of the raw drug materials per tablet (200 mg)

| Component | amount |
|---|---|
| Compound No. 46 | 2 mg |
| Calcium carboxymethyl cellulose | 5 mg |
| Lactose #100 (100 mesh) | 155.5 mg |
| Hydroxypropyl cellulose | 5 mg |
| Kollidon VA64 (BASF AG) | 30 mg |
| Magnesium stearate | 2.5 mg |

SYNTHETIC EXAMPLES

Hereinbelow, synthetic examples for the derivative of the compounds represented by the above formula (1) will be described.

EXAMPLE 1

Preparation of 13-Methylberberine (Compound No. 1)

3 G of 8-acetonyldihydroberberine and 15 ml of methyl iodide were dissolved in 100 ml of dichloromethane and reacted for 3 hours in an autoclave by heating to 100° C. The undissolved by-products were filtered off and the filtrate was distilled under reduced pressure to remove the solvent and the remaining methyl iodide. The residue was then recrystallized from methanol to give 1.53 g of titled compound as a yellow crystal (m.p.: 168° C.).

$^1$H-NMR (300 MHz, DMSO-$d_6$) δ: 2.92(s, 3H), 3.15(m, 2H), 4.09(s, 3H), 4.10(s, 3H), 4.80(m, 2H), 6.18(s, 2H), 7.15(s, 1H), 7.48(s, 1H), 8.19(d, J=9.0 Hz, 1H), 8.20(d, J=9.0 Hz, 1H), 9.89(s, 1H).

EXAMPLE 2

Preparation of 2,3-Dihydroxy-13-methylberberine (Compound No. 2)

0.4 G of 13-methylberberine and 1.2 g of anhydrous aluminum chloride were poured into a 100 ml round bottom flask. After dissolving the mixture by adding 40 ml of benzene into the flask, the solution was refluxed for 5 hours. Then, benzene was distilled off under reduced pressure. 40 ml of 1.2N hydrochloric acid was added to the mixture and the resulting reaction mixture was refluxed for 1 hour. After cooling the reaction mixture, the precipitate produced was filtered and then recrystallized from methanol to give 0.16 g of titled compound as light orange crystal (m.p.: 145° C.)

$^1$H-NMR (300 MHz, DMSO-$d_6$) δ: 2.91(s, 3H), 3.02(m, 2H), 3.84(s, 3H), 4.03(s, 3H), 4.74(m, 2H), 6.90(s, 1H), 7.33(s, 1H), 7.80(d, J=9.0 Hz, 1H), 8.05(d, J=9.0 Hz, 1H), 9.82(s, 1H), 10.05(s, 1H).

EXAMPLE 3

Preparation of 2,3,9,10-Tetrahydroxyberberine (Compound No. 3)

0.4 G of berberine and 2 g of anhydrous aluminum chloride were poured into a 100 ml round bottom flask. After dissolving the mixture by adding 40 ml of o-xylene into the flask, the solution was refluxed for 3 hours. Then, o-xylene was distilled off under reduced pressure. 40 ml of 1.2N hydrochloric acid was added to the mixture and the resulting reaction mixture was refluxed for 1 hour. After cooling the reaction mixture, the precipitate produced was filtered and recrystallized from methanol to give 0.24 g of the titled compound as a light orange crystal (m.p.: 163° C.).

$^1$H-NMR (300 MHz, CD$_3$OD) δ: 3.15(m, 2H), 4.75(m, 2H), 6.80(s, 1H), 7.47(s, 1H), 7.60(d, J=9.0 Hz, 1H), 7.72(d, J=9.0 Hz, 1H), 8.43(s, 1H), 9.66(s, 1H).

EXAMPLE 4

Preparation of 2,3,9,10-Tetrahydroxy-13-methylberberine (Compound No. 4)

0.6 G of 13-methylberberine and 3 g of anhydrous aluminum chloride were introduced into a 100 ml round bottom flask and then dissolved in 50 ml of toluene. After the solution was refluxed for 1 hour, toluene was distilled off under reduced pressure. 200 ml of 0.8N hydrochloric acid was added thereto and the solution was refluxed for 1 hour. The precipitate produced after cooling the reaction mixture was filtered and then recrystallized from methanol to give 0.3 g of the titled compound as a light orange crystal (m.p.: 255° C.).

$^1$H-NMR (300 MHz, DMSO-$d_6$) δ: 2.84(s, 3H), 3.00(m, 2H), 4.74(m, 2H), 6.86(s, 1H), 7.28(s, 1H), 7.72(d, J=9.0 Hz, 1H), 7.86(d, J=9.0 Hz, 1H), 9.40(s, 1H), 9.79(s, 1H), 9.87(s, 1H), 10.83(br, 1H).

EXAMPLE 5

Preparation of 2,3,9,10-Tetraethoxy-13-ethylberberine (Compound No. 5)

1.1 G of 2,3,9,10-tetrahydroxy-13-ethylberberine and 3.74 g of ethyl iodide were introduced into a 100 ml round bottom flask and then dissolved in 50 ml of acetonitrile. After 2.5 g of potassium carbonate were added thereto, the solution was refluxed for 5 hours. Undissolved by-products were filtered off and the filtrate was concentrated under reduced pressure to remove acetonitrile. The residue was adsorbed on celite, and then, purified by column chromatography eluting with methano/dichloromethane (1:10) to give 0.75 g of the titled compound as a white crystal (m.p.: 255° C.).

$^1$H-NMR (300 MHz, CDCl$_3$) δ: 1.39(s, 3H), 1.46(m, 2H), 3.12(m, 2H), 4.13(m, 12H), 4.41(m, 8H), 4.91(m, 2H), 7.19(s, 1H), 7.29(s, 1H), 8.19(d, 2H), 9.82(s, 1H).

EXAMPLE 6

Preparation of 13-Ethylberberine (Compound No. 6)

1.5 G of 8-acetonylberberine and 7.5 ml of ethyl bromide were dissolved in 100 ml of dichloromethane. The solution was then heated to 100° C. in an autoclave for 5 hours. Undissolved by-products were filtered off, and filtrate was concentrated under reduced pressure to remove solvent and the remaining ethyl bromide. The residue was recrystallized from methanol to give 0.83 g of the titled compound as a white crystal (m.p.: 230° C.).

$^1$H-NMR (300 MHz,DMSO-$d_6$) δ: 1.47(t, J=7.5 Hz, 3H), 3.09(m, 2H), 3.36(q, J=7.5 Hz, 2H), 4.10(s, 6H), 4.80(m, 2H), 6.19(s, 2H), 7.17(s, 1H), 7.30(s, 1H), 8.21(ABq, J=9.0 Hz, 2H), 9.90(s, 1H).

EXAMPLE 7

Preparation of 2,3,9,10-Tetrahydroxy-13-ethylberberine (Compound No. 7)

7.0 G of 13-ethylberberine and 21.0 g of anhydrous aluminum chloride were introduced into a 250 ml round bottom flask and then dissolved in 100 ml of toluene. After the solution was refluxed for 3 hours, toluene was distilled off under reduced pressure. 200 ml of 7% hydrochloric acid was added thereto and the solution was refluxed for 1 hour. The precipitate produced after cooling the reaction mixture was filtered and then recrystallized from methanol to give 2.56 g of the titled compound as a light orange crystal (m.p.: 280° C.). $^1$H-NMR (300 MHz, DMSO-$d_6$) δ: 1.54(t, J=7.5 Hz, 3H), 2.98(m, 2H), 3.25(q, J=7.5 Hz, 2H), 4.75(m, 2H), 6.86(s, 1H), 7.26(s, 1H), 7.78(d, J=8.7 Hz, 1H), 7.87(d, J=8.7 Hz, 1H), 9.52(br, 1H), 9.80(s, 1H), 9.83(br, 1H), 10.81(br, 1H), 10.90(br, 1H).

EXAMPLE 8

Preparation of 13-Ethylpalmatine (Compound No. 8)

1 G of 8-acetonyldihydropalnatine and 20 ml of ethyl iodide were dissolved in 100 ml of dichloromethane in a 250 ml round bottom flask. The solution was then refluxed for 3 hours. Undissolved by-products were filtered off, and the filtrate was concentrated under reduced pressure to remove excess ethyl iodide and solvent. The residue was recrystallized from methanol to give 0.55 g of the titled compound as a yellow crystal (m.p.: 186° C.).

$^1$H-NMR (300 MHz, CDCl$_3$) δ: 1.69(t, J=7.5 Hz, 3H), 3.20(m, 2H), 3.36(q, J=7.5 Hz, 2H), 3.71(m, 2H), 3.96(s, 3H), 4.00(s, 3H), 4.13(s, 3H), 4.25(s, 3H), 4.95(m, 2H), 7.00(s, 1H), 7.28(s, 1H), 8.03(d, J=9.0 Hz, 2H), 8.08(d, J=9.0 Hz, 1H), 10.00(s, 1H).

EXAMPLE 9

Preparation of 13-Allylberberine (Compound No. 9)

4.2 G of 8-acetonyldihydroberberine and 11 ml of allyl iodide were dissolved in 100 ml of dichloromethane in a 250 ml round bottom flask. The solution was then refluxed for 5 hours. Undissolved by-products were filtered off, and the filtrate was concentrated under reduced pressure to remove excess allyl iodide and solvent. The residue was recrystallized from methanol to give 1.72 g of the titled compound as a dark brown crystal (m.p.: 186° C.).

$^1$H-NMR (300 MHz, DMSO-$d_6$) δ: 3.13(m, 2H), 4.08(m, 2H), 4.08(s, 3H), 4.12(s, 3H), 4.85(m, 2H), 4.89(d, J=10.2 Hz, 1H), 5.38(d, J=10.2 Hz, 1H), 6.17(s, 2H), 6.45(m, 1H), 7.18(s, 1H), 7.36(s, 1H), 8.01(d, J=9.0 Hz, 1H), 8.20(d, J=9.0 Hz, 1H), 9.98(s, 1H).

EXAMPLE 10

Preparation of 2,3,9,10-Tetrahydroxy-13-allylberberine (Compound No. 10)

1.0 G of 13-allylberberine and 3.0 g of anhydrous aluminum chloride were introduced into a 50 ml round bottom flask and then dissolved in 20 ml of toluene. After the solution was refluxed for 5 hours, toluene was distilled off under reduced pressure. 40 ml of 7% hydrochloric acid was added thereto and the solution was refluxed for 1 hour. The precipitate produced after cooling the reaction mixture was filtered and recrystallized from methanol to give 0.43 g of the titled compound as a light orange crystal (m.p.: 234° C.).

$^1$H-NMR (300 MHz, CD$_3$OD) δ: 3.23(m, 2H), 4.08(m, 2H), 4.60(m, 2H), 5.12(d, J=10.2 Hz, 1H), 5.16(d, J=10.2 Hz, 1H), 6.71(s, 1H), 6.80(m, 1H), 7.76(s, 1H), 7.83(ABq, 2H), 8.86(s, 1H), 9.67(s, 1H), 10.22(s, 1H), 10.70(s, 1H), 10.78(s, 1H).

EXAMPLE 11

Preparation of 13-n-propylpalmatine (Compound No. 11)

0.5 G of 8-acetonyldihydropalmatine and 0.43 g of propyl iodide were introduced into a 100 ml round bottom flask and then dissolved in 50 ml of dioxane. The solution was refluxed for 4 hours. Undissolved by-products were filtered off and the filtrate was then concentrated under reduced pressure to remove dioxane. The residue was adsorbed on celite, and then, purified by column chromatography eluting with methanol/dichloromethane (1:10) to give 0.25 g of the titled compound as a yellow crystal (m.p.: 190° C.).

$^1$H-NMR (300 MHz, DMSO-$d_6$) δ: 1.05(t, J=7.0 Hz, 3H), 1.10(m, 2H), 1.83(m, 2H),3.08(m, 2H), 3.87(s, 3H), 3.89(s, 3H), 4.09(s, 3H), 4.10(s, 3H), 4.92(m, 2H), 7.19(s, 1H), 7.23(s, 1H), 8.20(ABq, 2H), 9.96(s, 1H).

EXAMPLE 12

Preparation of 13-n-butylpalmatine (Compound No. 12)

1.0 G of 8-acetonyldihydropalmatine and 9.2 g of butyl iodide were introduced into a 50 ml round bottom flask and then dissolved in 10 ml of acetonitrile. The solution was refluxed for 5 hours. Undissolved by-products were filtered off and the filtrate was then concentrated under reduced pressure to remove acetonitrile. The residue was adsorbed on celite, and then, purified by column chromatography eluting with methanol/dichloromethane (1:10) to give 0.42 g of the titled compound as a yellow crystal (m.p.: 170° C.).

$^1$H-NMR (300 MHz, DMSO-$d_6$) δ: 0.95(t, J=7.5 Hz, 3H), 1.47(m, 2H), 1.82(m, 2H), 3.14(m, 2H), 3.31(m, 2H), 3.81(s, 3H), 3.84(s, 3H), 4.01(s, 6H), 4.83(m, 2H), 7.20(s, 1H), 7.31(s, 1H), 8.23(ABq, 2H), 9.89(s, 1H).

EXAMPLE 13

Preparation of 13-(cyclopropylmethyl)palmatine (Compound No. 13)

1.0 G of 8-acetonyldihydropalmatine, 6.7 g of cyclopropylmethyl bromide and 1.14 g of sodium iodide were introduced into a 50 ml round bottom flask and then dissolved in 10 ml of acetonitrile. The solution was refluxed for 3 hours. Undissolved by-products were filtered off, and the filtrate was then concentrated under reduced pressure to remove acetonitrile. The residue was adsorbed on celite, and then, purified by column chromatography eluting with methanol/dichloromethane (1:10) to give 0.37 g of the titled compound as a yellow crystal (m.p.: 230° C.).

$^1$H-NMR (300 MHz, CDCl$_3$) δ: 0.42(m, 2H), 0.78(m, 2H), 1.04(m, 1H), 3.25(m, 2H), 3.38(d, J=6.0 Hz,2H), 3.98(s, 3H), 4.00(s, 3H), 4.05(s, 3H), 4.41(s, 3H), 5.18(m, 2H), 6.96(s, 1H), 7.45(s, 1H), 7.89(d, J=9.0 Hz, 1H), 8.17(d, J=9.0 Hz, 1H), 10.32(s, 1H).

EXAMPLE 14

Preparation of 13-n-octylpalmatine (Compound No. 14)

1.0 G of 8-acetonyldihydropalmatine, 9.6 g of octyl bromide and 1.14 g of sodium iodide were introduced into a 50 ml round bottom flask and then dissolved in 10 ml of acetonitrile. The solution was refluxed for 3 hours. Undissolved by-products were filtered off and the filtrate was then concentrated under reduced pressure to remove acetonitrile. The residue was adsorbed on celite, and then, purified by column chromatography eluting with methanol/ dichloromethane (1:10) to give 0.43 g of the titled compound as a yellow crystal (m.p.: 128° C.).

$^1$H-NMR (300 MHz, CDCl$_3$) δ: 0.89(t, J=7.0 Hz, 3H), 1.28(m, 6H), 1.63(m, 4H), 1.98(m,2H),3.27(m, 4H), 3.94(s, 3H), 4.01(s, 3H), 4.06(s, 3H), 4.40(s, 3H), 5.19(m, 2H), 6.95(s, 1H), 7.21(s, 1H), 7.88(ABq, 2H), 10.38(s, 1H).

EXAMPLE 15

Preparation of 13-(cyclohexylmethyl)palmatine (Compound No. 15)

1.0 G of 8-acetonyldihydropalmatine, 8.8 g of cyclohexylmethyl bromide and 1.14 g of sodium iodide were introduced into a 50 ml round bottom flask and then dissolved in 10 ml of acetonitrile. The solution was refluxed for 3 hours. Undissolved by-products were filtered off and filtrate was then concentrated under reduced pressure to remove acetonitrile. The residue was adsorbed on celite, and then, purified by column chromatography eluting with methanol/ dichloromethane (1:10) to give 0.47 g of the titled compound as a yellow crystal (m.p.: 198° C.).

$^1$H-NMR (300 MHz, CDCl$_3$) δ: 0.99 1.62(m, 1H), 3.21 (m, 2H), 3.46(d, J=7.5 Hz, 2H), 3.89(s, 3H), 4.01(s, 3H), 4.10(s, 3H), 4.40(s, 3H), 5.17(m, 2H), 6.94(s, 1H), 7.21(s, 1H), 7.87(ABq, 2H), 7.81(m, 1H), 10.38(s, 1H).

EXAMPLE 16

Preparation of 13-Iodopropylpalmatine (Compound No. 16)

1.0 G of 8-acetonyldihydropalmatine, and 7.4 g of 1,3-diiodopropane were introduced into a 50 ml round bottom flask and then dissolved in 30 ml of acetonitrile. The solution was refluxed for 6 hours. Undissolved by-products were filtered off and the filtrate was then concentrated under reduced pressure to remove acetonitrile. The residue was adsorbed on celite, and then, purified by column chromatography eluting with methanoll dichloromethane (1:10) to give 0.6 g of the titled compound as a brown crystal (m.p.: 156° C.).

$^1$H-NMR (300 MHz, CDCl$_3$) δ: 2.34(m, 2H), 3.26(m, 4H), 3.58(m, 2H), 3.98(s, 3H), 4.01(s, 3H), 4.09(s, 3H), 4.38(s, 3H), 5.10(m, 2H), 6.92(s, 1H), 7.20(s, 1H),7.88(d, J=9.0 Hz, 1H),7.98(d, J=9.0 Hz, 1H), 10.32(s, 1H).

EXAMPLE 17

Preparation of 2,3,9,10-Tetra-n-butoxyprotoberberine (Compound No. 17)

2.0 G of 2,3,9,10-tetrahydroxyberberine and 9.1 g of butyl iodide were introduced into a 250 ml round bottom flask and then dissolved in 100 ml of acetonitiile. 5.34 G of potassium carbonate were added thereto and the solution was then refluxed for 7 hours. Undissolved by-products were filtered off and the filtrate was then concentrated under reduced pressure to remove acetonitrile. The residue was adsorbed on celite, and then, purified by column chromatography eluting with methanol/dichloromethane (1:10) to give 1.51 g of the titled compound as a yellow crystal (m.p.: 180° C.).

$^1$H-NMR (300 MHz, DMSO-d$_6$) δ: 1.02(t, J=7.5 Hz, 12H), 1.48~1.62(m, 4H), 1.80~2.04(m, 4H), 3.30(m, 2H), 4.12(t, J=7.5 Hz, 2H), 4.18(t, J=7.5 Hz, 2H), 4.19(t, J=7.5 Hz, 2H), 4.51(t, J=7.5 Hz, 2H), 5.10(m, 2H), 6.72(s, 1H), 7.39(s, 1H), 7.68(d, J=9.0 Hz, 1H), 7.98(d, J=9.0 Hz, 1H), 8.52(s, 1H), 9.88(s, 1H).

EXAMPLE 18

Preparation of 13-(1,3-dioxane-2-yl)ethylpalmatine (Compound No. 18)

1.0 G of 8-acetonyldihydropalmatine and 3.4 ml of 2-(bromoethyl)-1,3-dioxane were introduced into a 50 ml round bottom flask and then dissolved in 20 ml of acetonitrile. The solution was refluxed for 6 hours. Undissolved by-products were filtered off and the filtrate was then concentrated under reduced pressure to remove acetonitrile. The residue was adsorbed on celite, and then, purified by column chromatography eluting with methanol/dichloromethane (1:10) to give 0.62 g of the titled compound as a yellow crystal (m.p.: 146° C.).

$^1$H-NMR (300 MHz, DMSO-d$_6$) δ: 1.37(d, J=13.5 Hz, 1H), 1.84(m, 1H), 2.08(m, 2H), 3.11(m, 2H), 3.43(m, 2H), 3.73(t, J=13.5 Hz, 2H), 3.89(s, 6H),4.00~4.05(m, 2H), 4.09 (s, 3H), 4.11(s, 3H), 4.78(m, 3H), 7.18(s, 1H), 7.32(s, 1H), 8.16(d, J=9.6 Hz, 1H), 8.26(d, J=9.6 Hz, 1H), 9.92(s, 1H).

EXAMPLE 19

Preparation of 13-Ethoxycrbonylpalmatine (Compound No. 19)

1.0 G of 8-acetonyldihydropalmatine, and 2.65 g of ethyl chloroformate were introduced into a 50 ml round bottom flask and then dissolved in 10 ml of acetonitile. The solution was refluxed for 6 hours. Undissolved by-products were filtered off and the filtrate was then concentrated under reduced pressure to remove acetonitrile. The residue was adsorbed on celite, and then, purified by column chromatography eluting with methanol/dichloromethane (1:10) to give 0.28 g of the titled compound as a yellow crystal (m.p.: 92° C.).

$^1$H-NMR (300 MHz, CDCl$_3$) δ: 1.19(t, J=7.5 Hz, 3H), 3.38(m, 2H), 3.88(s, 3H), 4.02(s, 3H), 4.08(s, 3H), 4.40(q, J=7.5 Hz, 2H), 4.42(s, 3H), 5.38(m, 2H), 6.89(s, 1H), 7.21(s, 1H), 7.73(d, J=9.0 Hz, 1H), 7.88(d, J=9.0 Hz, 1H), 10.82(s, 1H).

EXAMPLE 20

Preparation of 13-Ethoxycarbonylmethylpalmatine (Compound No. 20)

1.0 G of 8-acetonyldihydropalmatine, and 3.0 ml of ethyl chloroacetate were introduced into a 100 ml round bottom flask and then dissolved in 50 ml of acetonitrile. The solution was refluxed for 6 hours. Undissolved by-products were filtered off and the filtrate was then concentrated under reduced pressure to remove acetonitrile. The residue was adsorbed on celite, and then, purified by column chromatography eluting with methanol/dichloromethane (1:10) to give 0.25 g of the titled compound as a yellow crystal (m.p.: 200° C.).

$^1$H-NMR (300 MHz, DMSO-d$_6$) δ: 1.25(t, J=7.2 Hz, 3H), 2.02(m,2H), 3.18(m, 2H), 3.77(s, 3H), 3.90(s, 3H), 4.10(s, 3H), 4.12(s, 3H), 4.23(q, J=7.2 Hz, 2H), 4.51(s, 2H), 4.88 (m, 2H), 7.21(s, 1H), 7.22(s, 1H), 8.02(d, J=9.0 Hz, 1H), 8.23(d, J=9.0 Hz, 1H), 10.00(s, 1H).

EXAMPLE 21

Preparation of 13-Carboxymethylpalmatine (Compound No. 21)

0.45 G of 13-ethoxycarbonylpalmatine and 0.5 g of sodium hydroxide were introduced into a 50 ml round bottom flask and then dissolved in 30 ml of 80% methanol. The solution was refluxed for 4 hours. Concentrated hydrochloric acid was added dropwise thereto until the solution become acidic and then the solution was extracted with dichloromethane. The extract was dried with magnesium sulfate, filtered and concentrated. The residue was purified by column chromatography eluting with methanol/ dichloromethane (1:10) to give 0.15 g of the titled compound as a faint yellow crystal (m.p.: 198° C.).

$^1$H-NMR (300 MHz, DMSO-d$_6$) δ3.18(m, 2H), 3.78(s, 3H), 3.84(s, 3H), 4.08(s, 3H), 4.10(s, 3H), 4.37(s, 2H), 4.83(m, 2H), 7.20(s, 1H), 7.30(s, 1H), 8.06(d, J=9.0 Hz, 1H), 8.23(d, J=9.0 Hz, 1H), 9.98(s, 1H).

EXAMPLE 22

Preparation of 13-(1-methoxycarbonylethyl) berberine (Compound No. 22)

1.0 G of 8-acetonyldihydroberberine, and 4.2 g of methyl 2-bromopropionate were introduced into a 100 ml round bottom flask and then dissolved in 50 ml of chloroform. The solution was refluxed for 3 hours. Undissolved by-products were filtered off and the filtrate was then concentrated under reduced pressure to remove chloroform. The residue was adsorbed on celite, and then, purified by column chromatography eluting with methanol/dichloromethane (1:10) to give 0.38 g of the titled compound as a light yellow crystal (m.p.: 187° C.).

$^1$H-NMR (300 MHz, DMSO-d$_6$) δ: 1.58(d, J=7.5 Hz, 3H), 3.10(m, 2H), 4.03(s, 3H), 4.09(s, 3H), 4.64(m, 1H), 4.98(m, 2H), 6.19(s, 2H), 7.18(s, 1H), 7.27(s, 1H), 7.78(d, J=9.0 Hz, 1H), 8.23(d, J=9.0 Hz, 1H), 9.98(s, 1H).

EXAMPLE 23

Preparation of 13-α-(γ-lactonyl)berberine (Compound No. 23)

1.0 G of 8-acetonyldihydroberberine and 4.2 g of α-bromo-butyrolactone were introduced into a 100 ml round bottom flask and then dissolved in 50 ml of chloroform. The solution was refluxed for 3 hours. Undissolved by-products were filtered off and the filtrate was then concentrated under reduced pressure to remove chloroform. The residue was adsorbed on celite, and then, purified by column chromatography eluting with methanol/dichloromethane (1:10) to give 0.32 g of the titled compound as a yellow crystal (m.p.: 240° C.).

$^1$H-NMR (300 MHz, DMSO-d$_6$) δ: 2.67(m, 2H), 3.12(m, 2H), 4.06(s, 3H), 4.09(s, 3H), 4.56(dd, 1H), 4.76(m, 2H), 4.92(m, 1H), 5.12(t, 1H), 6.19(s, 2H), 7.22(s, 1H), 7.24(s, 1H), 7.65(d, J=9.0 Hz, 1H), 8.24(d, J=9.0 Hz, 1H), 10.00(s, 1H).

EXAMPLE 24

Preparation of 13-Ethoxycarbonylmethylberberine (Compound No. 24)

1.0 G of 8-acetonyldihydroberberine, 3.0 g of ethyl chloroacetate, and 3.75 g of sodium iodide were introduced into a 100 ml round bottom flask and then dissolved into 50 ml of chloroform. The solution was refluxed for 4 hours. Undissolved by-products were filtered off and the filtrate was then concentrated under reduced pressure to remove chloroform. The residue was adsorbed on celite, and then, purified by column chromatography eluting with methanol/ dichloromethane (1:10) to give 0.53 g of the titled compound as a pale yellow crystal (m.p.: 165° C.).

$^1$H-NMR (300 MHz, DMSO-d$_6$) δ: 1.22(t, J=7.5 Hz, 3H), 3.10(m, 2H), 4.08(s, 3H), 4.12(s, 3H), 4.23(q, J=7.5 Hz, 3H), 4.45(s, 2H), 4.82(m, 2H), 6.21(s, 2H), 7.18(s, 1H), 7.10(s, 1H), 8.01(d, J=9.0 Hz, 1H), 8.23(d, J=9.0 Hz, 1H), 10.00(s, 1H).

EXAMPLE 25

Preparation of 9-Hydroxyethylamino-13-ethylberberine (Compound No. 25)

0.5 G of 13-ethylpalmatine and 5 ml of ethanolamine were introduced into a 50 ml round bottom flask and then dissolved in 15 ml of ethanol. The solution was refluxed for 5 hours. Ethanol and unreacted ethanolamine were distilled off under reduced pressure. The residue was extracted with dichloromethane and then concentrated to remove solvent. The resulting residue was adsorbed on celite, and then, purified by column chromatography eluting with methanol/ dichloromethane (1:10) to give 0.16 g of the titled compound as a brown crystal (m.p.: 214° C.).

$^1$H-NMR (300 MHz, DMSO-d$_6$) δ: 1.51(t, J=7.5 Hz, 3H), 2.98(m, 2H), 3.12(m, 2H), 3.40(m, 4H), 3.78(s, 3H), 3.85(s, 3H), 3.86(s, 3H), 4.45(m, 2H), 6.64(d, J=9.0 Hz, 1H), 7.08(s, 1H), 7.21(s, 1H), 7.38(d, J=9.0 Hz, 2H), 9.22(s, 1H).

EXAMPLE 26

Preparation of 8-Acetonyldihydroberberine (Compound No. 26)

2.5 G of berberine, 2.5 ml of water and 13 ml of acetone were introduced into a 100 ml round bottom flask and a 50% sodium hydroxide solution was added dropwise to the mixture. The resulting reaction mixture was stirred at room temperature for 10 minutes. The precipitate was filtered and recrystallized from methanol to give 2.06 g of the titled compound as a brown crystal (m.p.: 130° C.).

$^1$H-NMR (300 MHz, DMSO-d$_6$) δ: 2.03(s, 3H), 2.30(dd, J=4.8, 14.4 Hz, 1H), 2.74(m, 2H), 2.93(dd, J=6.6, 14.4 Hz, 1H), 3.24(m, 3H), 3.76(s, 3H), 3.77(s, 3H), 5.21(dd, J=4.8, 6.6 Hz, 1H), 5.99(s, 2H), 6.00(s, 1H), 6.72(d, J=8.4 Hz, 1H), 6.75(s, 1H), 6.86(d, J=8.4 Hz, 1H), 7.24(s, 1H).

EXAMPLE 27

Preparation of 8-Methyldihydroberberine (Compound No. 27)

2.0 G of berberine, 2.13 g of methyl iodide, and 0.37 g of magnesium were introduced into a 250 ml round bottom flask and then dissolved in 150 ml of anhydrous ether. After refluxing for 1 hour, the solution was dried. Distilled water was then added to it while stirring. After the resulting solution was filtered, the filtrate was freeze dried. The residue was extracted with dichloromethane and then distilled off under reduced pressure to remove the solvent. 1.13 g of the titled compound was obtained as a dark green crystal (m.p.: 96° C.).

$^1$H-NMR (300 MHz, DMSO-d$_6$) δ: 1.06(d, J=6.3 Hz, 3I), 2.79(m, 3I), 3.30(m, 2H), 3.77(s, 3H), 3.78(s, 3H), 4.81(q, 1H), 5.93(s, 1H), 5.99(d, 2H), 6.68(d, J=8.7 Hz, 1H), 6.77(s, 1H), 6.82(d, J=8.7 Hz, 1H), 7.25(s, 1H).

EXAMPLE 28

Preparation of 8-Ethyldihydroberberine (Compound No. 28)

2.0 G of berberine, 1.51 ml of ethyl iodide, and 0.45 g of magnesium were introduced into a 250 ml round bottom flask and then dissolved in 150 ml of anhydrous ether. After refluxing for 1 hour, the solution was dried. Distilled water was then added to it while stirring. After the resulting solution was filtered, the filtrate was freeze dried. The residue was extracted with dichloromethane and the solvent was then distilled off under reduced pressure. 1.42 g of the titled compound was obtained as a dark brown crystal (m.p.: 90° C.).

$^1$H-NMR (300 MHz, DMSO-d$_6$) δ: 0.72(t, J=7.5 Hz, 3H), 1.61(m, 2H), 2.76(m, 2H), 3.30(m, 2H), 3.76(s, 6H), 4.63 (dd, 1H), 5.83(s, 1H), 5.99(d, J=1.2 Hz, 1H), 6.00(d, J=1.2 Hz, 1H), 6.67(d, J=8.1 Hz, 1H), 6.77(s, 1H), 6.83(d, J=8.1 Hz, 1H), 7.22(s, 1H).

EXAMPLE 29

Preparation of 8-n-propyldiydroberberine (Compound No. 29)

2.0 G of berberine, 1.8 ml of propyl iodide, and 0.457 g of magnesium in a 250 ml round bottom flask were well mixed with 150 ml of anhydrous ether. After refluxing for 1 hour, the solution was dried. Distilled water was then added to it while stirrng. After the resulting solution was filtered, the filtrate was freeze dried. The residue was extracted with dichloromethane and the solvent was then distilled off under reduced pressure to give 1.3 g of the titled compound as a yellow crystal (m.P.: 90° C.).

$^1$H-NMR (300 MHz, DMSO-d$_6$) δ: 0.76(t, J=7.5 Hz, 3H), 1.1 8(m, 2H), 1.58(m, 2H), 2.75(m, 2H), 3.31(m, 2H), 3.77(s, 6H), 4.67(dd, 1H), 5.85(s, 1H), 5.99(d, J=1.2 Hz, 1H), 6.00(d, J=1.2 Hz, 1H), 6.67(d, J=8.4 Hz, 1H), 6.76(s, 1H), 6.82(d, J=8.4 Hz, 1H), 7.23(s, 1H).

EXAMPLE 30

Preparation of 8-n-butyldihydroberberine (Compound No. 30)

2.0 G of berberine, 1.90 ml of butyl chloride and 0.37 g of magnesium in a 250 ml round bottom flask were well mixed with 150 ml of anhydrous ether and then refluxed for 3 hours. After drying the solution, distilled water was then added to it while stirring. After the resulting solution was filtered, the filtrate was freeze dried. The residue was extracted with dichloromethane and the solvent was then distilled off under reduced pressure to give 1.24 g of the titled compound as a brown crystal (m.p.: 68° C.) $^1$H-NMR (300 MHz, DMSO-d$_6$) δ: 0.75(t, J=7.5 Hz, 3H), 1.17(m, 4H), 1.59(m, 2H), 2.79(m, 2H), 3.30(m, 2H), 3.77(s, 6H), 4.67(dd, 1H), 5.86(s, 1H), 5.99(d, J=0.6 Hz, 1H), 6.00(d, J=0.6 Hz, 1H), 6.67(d, J=8.1 Hz, 1H), 6.76(s, 1H), 6.82(d, J=8.1 Hz, 1H), 7.23(s, 1H).

EXAMPLE 31

Preparation of 8-Cyclohexylmethyldihydroberberine (Compound No. 31)

2.0 G of berberine, 2.51 ml of cyclohexylmethyl bromide and 0.37 g of magnesium in a 250 ml round bottom flask were well mixed with 150 ml of anhydrous ether, and then, refluxed for 1 hour. After drying the solution, distilled water was then added to it while stirring. After the resulting solution was filtered, the filtrate was freeze dried. The residue was extracted with dichloromethane and the solvent was then distilled off under reduced pressure to give 1.66 g of the titled compound as a brown crystal. (m.p.: 107° C.).

$^1$H-NMR (300 MHz, DMSO-d$_6$) δ: 0.82(m, 2H), 1.14(m, 8H), 1.63(m, 2H), 2.81(m, 3H), 3.32(m, 2H), 3.76(s, 3H), 3.78(s, 3H), 4.62(dd, 1H), 5.92(s, 1H), 5.99(d, 2H), 6.66(d, J=8.1 Hz, 1H), 6.76(s, 1H), 6.81(d, J=8.1 Hz, 1H), 7.23(s, 1H).

EXAMPLE 32

Preparation of 8-i-propyldihydroberberine (Compound No. 32)

2.0 G of berberine, 1.8 ml of isopropyl iodide and 0.37 g of magnesium in a 250 ml round bottom flask were well mixed with 150 ml of anhydrous ether and was then refluxed for 3 hours. After drying the solution, distilled water was then added to it while stirring. After the resulting solution was filtered, the filtrate was freeze dried. The residue was extracted with dichloromethane and the solvent was then distilled off under reduced pressure to give 0.76 g of the titled compound as a brown crystal (m.p.: 98° C.)

$^1$H-NMR (300 MHz, DMSO-d$_6$) δ: 0.80(d, J=6.6 Hz, 3H), 0.82(d, J=6.6 Hz, 3H), 1.87(m, 1H), 2.68(m, 1H), 2.97(m, 1H), 3.75(s, 3H), 3.77(s, 3H). 4.48(d, 1H), 5.89(s, 1H), 5.99(s, 2H), 6.67(d, J=8.1 Hz, 1H), 6.75(s, 1H), 6.81(d, J=8.1 Hz, 1H), 7.25(s, 1H).

EXAMPLE 33

Preparation of 8-Methyldihydropalmatine (Compound No. 33)

2.0 G of palmatine, 1.21 ml of methyl iodide and 0.45 g of magnesium in a 250 ml round bottom flask were well mixed with 150 ml of anhydrous ether, and then, refluxed for 3 hours. After drying the solution, distilled water was then added to it while stirring. After the resulting solution was filtered, the filtrate was freeze dried. The residue was extracted with dichloromethane and the solvent was then distilled off under reduced pressure to give 0.64 g of the titled compound as a brown crystal (m.p.: 75° C.).

$^1$H-NMR (300 MHz, DMSO-d$_6$) δ: 1.02(d, 3H), 2.81(m, 2H), 3.27(m, 2H), 3.76(s, 3H), 3.77(s, 3H), 3.78(s, 3H), 3.81(s, 3H), 4.78(q, 1H), 6.00(s, 1H), 6.68(d, J=8.1 Hz, 1H), 6.79(s, 1H), 6.81(d, J=8.1 Hz, 1H), 7.20(s 1H).

EXAMPLE 34

Preparation of 8-Ethyldihydropalmatine (Compound No. 34)

2.0 G of palmatine, 2.9 ml of ethyl iodide and 0.9 g of magnesium in a 250 ml round bottom flask were well mixed with 150 ml of anhydrous ether, and then, refluxed for 1 hour. After drying the solution, distilled water was then added to it while stirring. After the resulting solution was filtered, the filtrate was freeze dried. The residue was extracted with dichloromethane and the solvent was then distilled off under reduced pressure to give 0.88 g of the titled compound as a brown crystal (m.p.: 86° C.).

$^1$H-NMR (300 MHz, DMSO-$d_6$) δ: 0.73(t, 3H), 1.61(m, 2H), 2.80(m, 2H), 3.47(m, 2H), 3.76(s, 3H), 3.77(s, 3H), 3.78(s, 3H), 3.81(s, 3H), 4.62(m, 1H), 5.89(s, 1H), 6.69(d, J=8.1 Hz, 1H), 6.79(s, 1H), 6.82(d, J=8.1 Hz, 1H), 7.20(s, 1H).

EXAMPLE 35

Preparation of 8-n-octyldihydropalmatine (Compound No. 35)

2.0 G of berberine, 4.2 ml of octyl iodide and 0.45 g of magnesium in a 250 ml round bottom flask were well mixed with 150 ml of anhydrous ether, and then, refluxed for 3 hours. After drying the solution, distilled water was then added to it while stirring. After the resulting solution was filtered, the filtrate was freeze dried. The residue was extracted with dichloromethane and the solvent was then distilled off under reduced pressure to give 0.92 g of the titled compound as a brown liquid (m.p.: room temperature).

$^1$H-NMR (300 MHz, DMSO-$d_6$) δ: 0.84(t, 3H), 1.19(m, 12H), 2.69(m, 2H), 2.79(m, 2H), 3.01(m, 2H), 3.74(s, 3H), 3.89(s, 3H), 4.78(dd, 1H), 6.06(s, 1H), 6.11(s, 2H), 7.00(s, 1H), 7.11(d, 1H), 7.19(d, 1H), 7.27(s, 1H).

EXAMPLE 36

Preparation of 8-Cyclopropyldihydropalmatine (Compound No. 36)

2.0 G of berberine, 1.42 ml of cyclopropyl iodide and 0.45 g of magnesium in a 250 ml round bottom flask were well mixed with 150 ml of anhydrous ether, and then, refluxed for 3 hours. After drying the solution, distilled water was then added to it while stirring. After the resulting solution was filtered, the filtrate was freeze dried. The residue was extracted with dichloromethane and the solvent was then distilled off under reduced pressure to give 0.71 g of the titled compound as a brown crystal (m.p.: 162° C.).

$^1$H-NMR (300 MHz, DMSO-$d_6$) δ: 0.42(m, 4H), 1.19(m, 1H), 2.80(m, 2H), 3.55(m, 2H), 3.73(s, 3H), 3.77(s, 3H), 3.91(m, 1H), 5.99(s, 1H), 6.00(d, 2H), 6.72(d, J=8.4 Hz, 1H), 6.77(s, 1H), 6.85(d, J=8.4 Hz, 1H), 7.30(s, 1H).

EXAMPLE 37

Preparation of 8-Acetonyl-13-ethyldihydropalmatine (Compound No. 37)

10 G of 13-ethylpalmatine, 50 ml of water and 10 ml of acetone were introduced into a 100 ml round bottom flask and 15 g of a 50% sodium hydroxide solution was added dropwise to the reaction mixture. The mixture was stirred at room temperature for 10 minutes. The precipitate was filtered and recrystallized from methanol to give 8.63 g of the titled compound as a white crystal (m.p.: 156° C.).

$^1$H-NMR (300 MHz, CDCl$_3$) δ: 1.33(t, J=7.2 Hz, 3H), 2.00(s, 3H), 2.23(dd, 1H), 2.80(m, 5H), 3.20(m, 1H), 3.33 (m, 1H), 3.87(s, 3H), 3.90(s, 3H), 3.91(s, 3H), 3.93(s, 3H), 5.12(dd, 1H), 6.67(s, 1H), 6.87(d, J=8.1 Hz, 1H), 7.03(d, J=8.1 Hz, 1H), 7.10(s, 1H).

EXAMPLE 38

Preparation of 8-(butan-2-one-1-yl)-13-ethyldihydropalmatine (Compound No. 38)

10 G of 13-ethylpalmatine, 50 ml of water and 12 ml of ethylmethylketone were introduced into a 100 ml round bottom flask, and 15 g of a 50% sodium hydroxide solution was added dropwise to the mixture. The mixture was stirred at room temperature for 10 minutes. The precipitate was filtered and recrystallized from methanol to give 814 g of the titled compound as a white crystal (m.p.: 127° C.).

$^1$H-NMR (300 MHz, DMSO-$d_6$) δ: 0.79(m, 3R), 1.25(m, 3H), 2.25(m, 2H), 2.70(m, 6H), 3.01(m, 1H), 3.28(m, 1H), 3.77(s, 3H), 3.78(s, 3H), 3.79(s, 3H), 3.80(s, 3H), 5.14(dd, 1H), 6.85(s, 1H), 6.95(d, J=8.1 Hz, 1H), 6.96(d, J=8.1 Hz, 1H), 7.00(s, 1H).

EXAMPLE 39

Preparation of 8-(3-methylbutan-2-one-1-yl)-13-ethyldihydro palmatine (Compound No. 39)

10 G of 13-ethylpalmatine, 50 ml of water and 13 ml of i-propylmethyl ketone were introduced into a 100 ml round bottom flask, and 15 g of a 50% sodium hydroxide solution was added dropwise to the mixture. The mixture was stirred at room temperature for 10 minutes. The precipitate was filtered and recrystallized from methanol to give 7.84 g of the titled compound as a white crystal (m.p.: 72 C).

$^1$H-NMR (300 MHz, CDCl$_3$) δ: 0.89(d, J=6.9 Hz, 3H), 0.95(d, J=6.9 Hz, 3H), 1.33(t, 3H), 2.20(m, 1H), 2.40(m, 1H), 2.79(m, 4H), 3.12(s, 2H), 3.37(m, 3H), 3.87(s, 3H), 3.90(s, 3H), 3.90(s, 3H), 3.92(s, 3H), 5.31(dd, 1H), 6.66(s, 1H), 6.86(d, J=9.0 Hz, 1H), 7.04(d, J=9.0 Hz, 1H), 7.09(s, 1H).

EXAMPLE 40

Preparation of 8-(4-methylpentan-2-one-1-yl)-13-ethyldihydropalmatine (Compound No. 40)

10 G of 13-ethylpalmatine, 50 ml of water and 15 ml of i-butylmethylketone were introduced into a 100 ml round bottom flask, and 15 g of a 50% sodium hydroxide solution was added dropwise to the mixture. The mixture was stirred at room temperature for 10 minutes. The precipitate was filtered and recrystallized from methanol to give 7.84 g of the titled compound as a white crystal (m.p.: 127° C.).

$^1$H-NMR (300 MHz, CDCl$_3$) δ: 0.79(m, 6H), 1.27(t, 3H), 1.97(m, 1H), 2.17(m, 2H), 2.25(m, 1H), 2.82(m, 5H), 3.18 (m, 1H), 3.36(m, 1H), 3.87(s, 3H), 3.91(s, 6H), 3.94(s, 3H), 5.26(dd, J=3.6, 8.1 Hz, 1H), 6.67(s, 1H), 6.86(d, J=8.7 Hz, 1H), 7.04(d, J=8.7 Hz, 1H), 7.10(s, 1H).

EXAMPLE 41

Preparation of 8-Cyanomethyl-13-ethyldihydropalmatine (Compound No. 41)

10 G of 13-ethylpalmatine, 50 ml of water and 10 ml of acetonitrile were introduced into a 100 ml round bottom flask, and 15 g of a 50% sodium hydroxide solution was added dropwise to the mixture. The mixture was stirred at room temperature for 10 minutes. The precipitate was filtered and recrystallized from methanol to give 8.09 g of the titled compound as a white crystal (m.p.: 147° C.).

$^1$H-NMR (300 MHz, CDCl$_3$) δ: 1.28(t, 3H), 2.75(m, 6H), 3.51(m, 1H), 3.91(s, 6H), 3.92(s, 3H), 3.95(s, 3H), 4.13(m,

1H), 5.61(s, 1H), 6.72(s, 1H), 7.03(s, 1H), 7.05(d, J=9.0 Hz, 1H), 7.16(d, J=9.0 Hz, 1H).

EXAMPLE 42

Preparation of 8-(cyclopentanon-2-yl)-13-ethyldihydropalmatine (Compound No. 42)

10 G of 13-ethylpalmatine, 50 ml of water and 15 ml of cyclopentanone were introduced into a 100 ml round bottom flask, and 15 g of a 50% sodium hydroxide solution was added dropwise to the mixture. The mixture was stirred at room temperature for 10 minutes. The precipitate was filtered and recrystallized from methanol to give 7.7 g of the titled compound as a white crystal (m.p.: 165° C.).
$^1$H-NMR (300 MHz, CDCl$_3$) δ: 1.22(t, 3H), 1.80(m, 8H), 2.70(m, 4H), 3.23(m, 1H), 3.88(s, 3H), 3.90(s, 3H), 3.94(s, 3H), 3.95(s, 3H), 5.50(d, 1H), 6.66(s, 1H), 6.86(d, J=8.7 Hz, 1H), 6.98(d, J=8.7 Hz, 1H), 7.07(s, 1H).

EXAMPLE 43

Preparation of 8-(cyclohexanon-2-yl)-13-ethyldihydropalmatine (Compound No. 43)

10 G of 13-ethylpalmatine, 50 ml of water and 15 ml of cyclohexanone were introduced into a 100 ml round bottom flask, and 15 g of a 50% sodium hydroxide solution was added dropwise to the mixture. The mixture was stirred at room temperature for 10 minutes. The precipitate was filtered and recrystallized from methanol to give 7.46 g of the titled compound as a white crystal (m.p.: 125° C.).
$^1$H-NMR (300 MHz, CDCl$_3$) δ: 1.24(t, 3H), 1.62(m, 5H), 2.30(m, 4H), 2.85(m, 4H), 3.20(m, 2H), 3.87(s, 6H), 3.91(s, 3H), 3.92(s, 3H), 5.67(d, J=1.8 Hz, 1H), 6.68(s, 1H), 6.85(d, J=8.7 Hz, 1H), 6.98(d, J=8.7 Hz, 1H), 7.03(s, 1H).

EXAMPLE 44

Preparation of 8-Acetonyl-13-ethyl-2,3,9,10-tetraethoxy-dihydroprotoberberine (Compound No. 44)

15 G of 13-ethyl-2,3,9,10-tetraethoxyprotoberberine, 10 ml of water and 15 ml of acetone were introduced into a 100 ml round bottom flask, and 20 g of a 50% sodium hydroxide solution was added dropwise to the mixture. The solution was stirred at room temperature for 10 minutes. The solvent was distilled off under reduced pressure to its half amount. The precipitate was filtered and recrystallized from methanol to give 7.06 g of the titled compound as a white crystal (m.p.: 108° C.).
$^1$H-NMR (300 MHz, CDCl$_3$) δ: 1.32(t, 3H), 1.42(m, 12H), 1.99(s, 3H), 2.30(m, 1H), 2.75(m, 4H), 3.20(m, 1H), 4.05(m, 10H), 5.26(dd, J=3.9, 7.5 Hz, 1H), 6.66(s, 1H), 6.83(d, J=8.7 Hz, 1H), 7.00(d, J=8.7 Hz, 1H), 7.10(s, 1H).

EXAMPLE 45

Preparation of 8-(3-methylbutan-2-one-1-yl)-13-ethyl-2,3,9,10-tetra ethoxydihydroprotoberberine (Compound No. 45)

15 G of 13-ethyl-2,3,9, 10-tetraethoxyprotoberberine, 10 ml of water and 60 ml of i-propyl methyl ketone were introduced into a 100 ml round bottom flask, and 20 g of a 50% sodium hydroxide solution was added dropwise to the mixture. The solution was stirred at room temperature for 10 minutes. The solvent was distilled off under reduced pressure to its half. The precipitate was filtered and recrystallized from methanol to give 6.78 g of the titled compound as a white crystal (m.p.: 103° C.).
$^1$H-NMR (300 MHz, DMSO-d$_6$) δ: 0.79(d, J=7.2 Hz, 3H), 0.86(d, J=6.9 Hz, 3H), 1.33(m, 15H), 2.09(dd, 1H), 2.60(m, 6H), 4.00(m, 10H), 5.21(dd, 1H), 6.81(s, 1H), 6.88(d, 1H), 6.91(d, 1H), 7.00(s, 1H).

EXAMPLE 46

Preparation of 13-Ethyldihydropalmatine (Compound No. 46)

0.8 G of 13-ethylpalmatine and 0.83 g of potassium carbonate in a 50 ml round bottom flask were dissolved in 30 ml of methanol. After the solution was cooled to 0° C. with ice, 0.05 g of sodium borohydride was slowly added dropwise to it. The solution was allowed to stand for 1 hour. The precipitate was filtered, and dissolved in ethyl acetate and then the mixture was washed with water. The organic layer was dried over magnesium sulfate, filtered and concentrated under reduced pressure to remove the solvent. The residue was recrystallized from methanol to give 0.57 g of the titled compound as a yellow crystal (m.p.: 122° C.)
$^1$H-NMR (300 MHz, CDCl$_3$) δ: 1.34(t, J=7.5 Hz, 3H), 2.81(m, 4H), 3.08(m, 2H), 3.85(s, 3H), 3.88(s, 3H), 3.91(s, 3H), 3.92(s, 3H), 4.27(s, 2H), 6.68(s, 1H), 6.84(d, J=8.4 Hz, 1H), 7.03(d, J=8.4 Hz, 1H), 7.17(s, 1H).

EXAMPLE 47

Preparation of 13-Ethyl-2,3,9,10-tetraethoxydihydroprotoberberine (Compound No. 47)

1.0 G of 13-ethyl-2,3,9,10-tetraethoxyprotoberberine and 0.83 g of potassium carbonate in a 50 ml round bottom flask were dissolved in 30 ml of methanol. After the solution was cooled to 0° C. with ice, 0.05 g of sodium borohydride was slowly added dropwise to it. The solution was allowed to stand for 1 hour. The solvent was distilled off under reduced pressure and the residue was extracted with dichloromethane. The organic phase was dried over magnesium sulfate, filtered and concentrated under reduced pressure to remove the solvent. The residue was recrystallized from methanol to give 0.70 g of the titled compound as a yellow crystal (m.p.: 103° C.)
$^1$H-NMR (300 MHz, CDCl$_3$) δ: 0.79(t, J=7.8 Hz, 3H), 1.38(m, 12H), 2.57(m, 2H),2.89(m, 1H),3.13(m, 2H), 3.47 (d, J=16.2 Hz, 1H), 3.68(m, 1H), 4.13(m, 8H), 4.23(d, J=16.2 Hz, 1H), 6.63(s, 1H), 6.73(s, 1H), 6.78(d, J=8.4 Hz, 1H), 6.85(d, J=8.4 Hz, 1H).

EXAMPLE 48

Preparation of 8-Methyl-13-ethyldihydropalmatine (Compound No. 48)

1.25 G of 13-ethylpalmatine in a 25 ml round bottom flask were dissolved in 15 ml of tetrahydrofuran. After the solution was cooled to 0° C. with ice, 1.5 ml of 3.0 M methylmagnesium chloride were slowly added using a syringe over 10 minutes. After stirring at 0° C. for 1.5 hours and at room temperature for 30 minutes, the reaction mixture was quenched by pouring water. The solvent was distilled off under reduced pressure. The residue was dissolved into dichloromethane, washed with water. The organic phase was dried over magnesium sulfate, filtered and concentrated under reduced pressure to remove the solvent. The residue was recrystallized from ethyl acetate/n-hexane to give 0.93 g of the titled compound as a yellow crystal (m.p.: 134° C.)

$^1$H-NMR (300 MHz, CDCl$_3$) δ: 1.10(d, J=6.3 Hz, 3H), 1.33(t, J=7.5 Hz, 3H), 2.75(m, 2H), 2.91(m, 2H), 3.26(m, 2H), 3.88(s, 3H), 3.91(s, 3H), 3.92(s, 3H), 3.93(s, 3H), 4.75(q, J=6.3 Hz, 1H), 6.69(s, 1H), 6.82(d, J=8.7 Hz, 1H), 7.04(d, J=8.7 Hz, 1H), 7.15(s, 1H).

EXAMPLE 49

Preparation of 8-Ethyl-13-ethyldihydropalmatine (Compound No. 49)

1.25 G of 13-ethylpalmatine in a 25 ml round bottom flask were dissolved into 15 ml of tetrahydrofuran. After the solution was cooled to 0° C. with ice, 6.0 ml of 1.0 M ethyl magnesium chloride were slowly added using a syringe over 10 minutes. After stirring at 0° C. for 1.5 hours and at room temperature for 30 minutes, the reaction mixture was quenched by pouring water. The solvent was distilled off under reduced pressure. The residue was dissolved into dichloromethane, washed with water. The organic phase was dried over magnesium sulfate, filtered and concentrated under reduced pressure to remove the solvent. The residue was recrystallized from ethyl acetate/n-hexane to give 1.0 g of the titled compound as a yellow crystal (m.p.: 153° C.)

$^1$H-NMR (300 MHz, CDCl$_3$) δ: 0.79(t, J=7.5 Hz, 3H), 1.30(t, J=7.5 Hz, 3H), 1.61(m, 2H), 2.70(m, 2H), 2.90(m, 2H), 3.33(m, 2H), 3.88(s, 3H), 3.90(s, 3H), 3.91(s, 3H), 3.93(s, 3H), 4.60(dd, 1H), 6.69(s, 1H), 6.84(d, J=8.7 Hz, 1H), 7.03(d, J=8.7 Hz, 1H), 7.12(s, 1H).

EXAMPLE 50

Preparation of 8-n-butyl-13-ethyldihydropalmatine (Compound No. 50)

1.25 G of 13-ethylpalmatine in a 25 ml round bottom flask were dissolved into 15 ml of tetrahydrofuran. After the solution was cooled to 0° C. with ice, 3.0 ml of 1.6 M n-butylmagnesium chloride were slowly added using a syringe over 10 minutes. After stirring at 0° C. for 1.5 hours and at room temperature for 30 minutes, the reaction mixture was quenched by pouring water. The solvent was distilled off under reduced pressure. The residue was dissolved into dichloromethane, washed with water. The organic phase was dried over magnesium sulfate, filtered and concentrated under reduced pressure to remove the solvent. The residue was recrystallized from ethyl acetate/n-hexane to give 1.3 g of the titled compound as a yellow crystal (m.p.: 112° C.)

$^1$H-NMR (300 MHz, CDCl$_3$) δ: 0.78(t, J=6.9 Hz, 3H), 1.19(m, 4H), 1.28(t, J=7.2 Hz, 3H), 1.59(m, 2H), 2.70(m, 2H), 2.91(m, 2H), 3.34(m, 2H), 3.88(s, 3H), 3.89(s, 3H), 3.91(s, 3H), 3.93(s, 3H), 4.61(dd, 1H), 6.69(s, 1H), 6.84(d, J=8.4 Hz, 1H), 7.03(d, J=8.4 Hz, 1H), 7.12(s, 1H).

INDUSTRIAL APPLICABILITY 7,8,13,13α-tetradehydrocoridaline which is a pharmacological ingredient of *Corydalis Turtschaninowii Besser* and the compounds of formula (1) can effectively inhibit sterol 14-reductase which is involved in the distal pathway of cholesterol biosynthesis, and thus, are especially effective in treating hypercholesterolemia.

The compounds of formula (1) above have the activities to decrease total cholesterol, LDL-cholesterol, and triglyceride levels and at the same time, to decrease glucose level in an animal test. Therefore, they are effective in diabetic hypercholesterolaemia and hyperlipidaemia.

Table 3 represents the relative activity for sterol 14-reductase of the compound of formula (1) as set forth in Table 1. Among the compounds of Table 1, Compound Nos. 5, 6, 8, 37, 38, 46 and 47 markedly inhibited the cholesterol biosynthesis in human HepG2 cell line compared with AY9944 which is a comparative drug. In the animal test with Syrian Golden Hamster, Compound Nos. 5, 8, 37 and 46 have markedly decreased total cholesterol, LDL-cholesterol, and triglyceride levels compared with lovastatin which is a commercially available comparative cholesterol-lowering agent.

TABLE 3

Relative In Vitro activity of the compound of formula (1)

| Compound No. | Enzyme Activity | Compound No. | Enzyme Activity |
|---|---|---|---|
| 1 | + + | 26 | + |
| 2 | + + | 27 | + |
| 3 | + | 28 | + |
| 4 | + + | 29 | + |
| 5 | + + + | 30 | + |
| 6 | + + + | 31 | + |
| 7 | + + | 32 | + |
| 8 | + + + | 33 | + |
| 9 | + | 34 | + |
| 10 | + | 35 | + |
| 11 | + + | 36 | + |
| 12 | + + | 37 | + + + |
| 13 | + | 38 | + + + |
| 14 | + | 39 | + + |
| 15 | + | 40 | + + |
| 16 | + + | 41 | + |
| 17 | + + | 42 | + |
| 18 | + | 43 | + |
| 19 | + | 44 | + + |
| 20 | + | 45 | + + |
| 21 | + | 46 | + + + |
| 22 | + | 47 | + + + |
| 23 | + | 48 | + |
| 24 | + | 49 | + |
| 25 | + + | 50 | + |

+: 100 μM or more of IC$_{50}$ value
+ +: 10–100 μM of IC$_{50}$ value
+ + +: 1 μM or below of IC$_{50}$ value

TABLE 4

| Group No. | n | Total cholesterol (mg/dl) | HDL cholesterol (mg/dl) | LDL cholesterol (mg/dl) | Trigly-ceride (mg/dl) | Glucose (mg/dl) |
|---|---|---|---|---|---|---|
| normal diet control | 5 | 126.6 ± 2.0 | 52.8 ± 4.2 | 42.2 ± 2.5 | 132.4 ± 25.3 | 182.2 ± 24.6 |
| normal diet + lovastatin 6.0 mg/kg/day | 5 | 97.4 ± 3.4 (−22.7%) | 51.4 ± 2.6 (−2.6%) | 29.9 ± 1.9 (−29.1%) | 182.6 ± 17.0 (−37.8%) | 184.6 ± 23.2 (+1.0%) |
| normal diet + comp. 8 6.0 mg/kg/day | 5 | 94.0 ± 6.6 (−25.4%) | 47.5 ± 3.0 (−1.8%) | 24.5 ± 1.8 (−42.0%) | 90.4 ± 8.9 (−31.7%) | 162.2 ± 11.3 (−10.9%) |
| normal diet + Comp. 5 6.0 mg/kg/day | 5 | 97.0 ± 5.6 (−23.5%) | 51.1 ± 3.0 (−3.2%) | 24.9 ± 3.0 (−41.2%) | 94.7 ± 11.5 (−28.5%) | 160.2 ± 20.9 (−12.4%) |
| normal diet + Comp. 37 6.0 mg/kg/day | 5 | 83.8 ± 5.6 (−33.5%) | 54.2 ± 3.0 (+2.0%) | 20.2 ± 2.0 (−52.1%) | 68.8 ± 11.5 (−48.1%) | 140.4 ± 15 (−23.0%) |
| normal diet + Comp. 46 6.0 mg/kg/day | 5 | 82.4 ± 5.4 (−34.6%) | 49.2 ± 2.9 (−6.8%) | 20.8 ± 2.3 (−50.7%) | 85.2 ± 11.0 (−35.6%) | 158.8 ± 16 (−12.7%) |

Meanwhile, the toxicity of the compounds of the present invention was investigated as follows: i.e., the compounds were suspended into propylene glycol and then orally administered into each of 5 male and female SD rats at the age of 5-weeks that were fasted for 12 hours. Under the usual breeding conditions, general symptoms, weight change and lethal case of the above rats were monitored for two weeks. At the dose over 2,000 mg/kg of the compound nos. 5, 37, and 46, general symptoms and the body weight change of the animals were normal and the lethal case was not observed. Rats were safe against the dose of 700 mg/kg of compound no. 8. The toxicity data for the representative compounds (Compound No. 5, 8, 37 and 46) is set forth in Table 5.

TABLE 5

| | Acute Toxicity (mg/kg) | | | |
|---|---|---|---|---|
| Comp. No. | animal | administration route | sex | $LD_{50}$ |
| Comp. 5 | rats | oral | male | >5,000 |
| | | | female | >5,000 |
| Comp. 8 | rats | oral | male | >925 |
| | | | female | >760 |
| Comp. 37 | rats | oral | male | >2,500 |
| | | | female | >2,000 |
| Comp. 46 | rats | oral | male | >3,000 |
| | | | female | >3,000 |

As evident from the above descriptions, the compound of formula (1) inhibits sterol 14-reductase which is an enze in the distal stage of the cholesterol biosynthesis, thereby being effective in treatment of hypercholesterolemia and hyperlipidaemia and safe in an aspect of toxicity.

What is claimed is:

1. A cholesterol biosynthesis inhibitor, which comprises: an extract which inhibits cholesterol biosynthesis in a cultured human liver cell culture (Hep G2 cell line), the extract obtained by extracting under reflux *Corydalis Turtschaninowii Besser* with a solvent selected from the group consisting of water, an alcohol, dichloromethane and a mixture thereof, and removing the solvent, the extract including a compound of chemical formula (1a) or a pharmaceutically acceptable salt thereof:

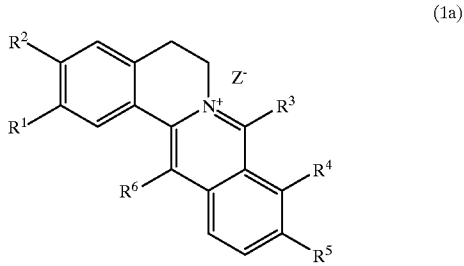

(1a)

wherein $R^1$ and $R^2$, which may be the same or different from each other, represent a hydroxy group or an alkoxy group having 1 to 4 carbon atoms or both of $R^1$ and $R^2$ represent a methylenedioxy group;

$R^3$ represents a hydrogen atom;

$R^4$ and $R^5$, which may be the same or different from each other, represent a hydroxy group, a hydroxyethylamino group or an alkoxy group having 1 to 4 carbon atoms;

$R^6$ represents a hydrogen atom, a branched alkyl group having 4 to 8 carbon atoms, a cyclic alkyl group having 3 to 8 carbon atoms, or a straight chain alkyl group having 8 carbon atoms, an alkenyl group having 3 to 8 carbon atoms, a cycloalkylalkyl group having 3 to 7 carbon atoms, a haloalkyl group having 1 to 4 carbon atoms, an ethoxycarbonyl group, an ethoxycarbonylmethyl group, a hydroxycarbonylmethyl group, a 1-ethoxycarbonylethyl group, or a 2-valerolactonyl group; and Z represents a halogen atom.

2. The cholesterol biosynthesis inhibitor according to claim 1, wherein said inhibitor is a sterol 14-reductase inhibitor.

3. A cholesterol biosynthesis inhibitor of chemical formula (1a) or a pharmaceutically acceptable salt thereof:

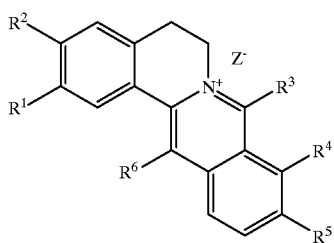

(1a)

wherein, $R^1$ and $R^2$, which may be the same or different from each other, represent a hydroxy group or an alkoxy group having 1 to 4 carbon atoms or both of $R^1$ and $R^2$ represent a methylenedioxy group;

$R^3$ represents a hydrogen atom;

$R^4$ and $R^5$, which may be the same or different from each other, represent a hydroxy group, a hydroxyethylamino group or an alkoxy group having 1 to 4 carbon atoms;

$R^6$ represents a hydrogen atom, a branched alkyl group having 4 to 8 carbon atoms, a cyclic alkyl group having 3 to 8 carbon atoms, or a straight chain alkyl group having 8 carbon atoms, an alkenyl group having 3 to 8 carbon atoms, a cycloalkylalkyl group having 3 to 7 carbon atoms, a haloalkyl group having 1 to 4 carbon atoms, an ethoxycarbonyl group, an ethoxycarbonylmethyl group, a hydroxycarbonylmethyl group, a 1-ethoxycarbonylethyl group, or a 2-valerolactonyl group; and Z represents a halogen atom.

4. The cholesterol biosynthesis inhibitor of chemical formula (1a) or the pharmaceutically acceptable salt thereof according to claim 3, wherein $R^1$, $R^2$, $R^4$ and $R^5$ each represents methoxy, $R^3$ represents a hydrogen atom, $R^6$ represents ethyl, and Z represents chloride.

5. The cholesterol biosynthesis inhibitor of chemical formula (1a) or the pharmaceutically acceptable salt thereof according to claim 3, wherein $R^1$, $R^2$, $R^4$ and $R^5$ each represents ethoxy, $R^3$ represents a hydrogen atom, $R^6$ represents ethyl, and Z represents chloride.

6. A pharmaceutical composition for treating hyperlipidaemia which comprises a compound of chemical formula (1a) or a pharmaceutically acceptable salt thereof as an active ingredient and a pharmaceutically acceptable excipient:

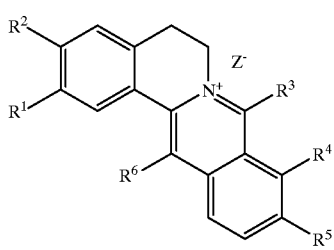

(1a)

wherein, $R^1$ and $R^2$, which may be the same or different from each other, represent a hydroxy group or an alkoxy group having 1 to 4 carbon atoms or both of $R^1$ and $R^2$ represent a methylenedioxy group;

$R^3$ represents a hydrogen atom;

$R^4$ and $R^5$, which may be the same or different from each other, represent a hydroxy group, a hydroxyethylamino group or an alkoxy group having 1 to 4 carbon atoms;

$R^6$ represents a hydrogen atom, a branched alkyl group having 4 to 8 carbon atoms, a cyclic alkyl group having 3 to 8 carbon atoms, or a straight chain alkyl group having 8 carbon atoms, an alkenyl group having 3 to 8 carbon atoms, a cycloalkylalkyl group having 3 to 7 carbon atoms, a haloalkyl group having 1 to 4 carbon atoms, an ethoxycarbonyl group, an ethoxycarbonylmethyl group, a hydroxycarbonylmethyl group, a 1-ethoxycarbonylethyl group, or a 2-valerolactonyl group; and Z represents a halogen atom.

7. A pharmaceutical composition for treating hyperlipidaemia which comprises a compound of formula (1b) or a pharmaceutically acceptable salt thereof and a pharmaceutically acceptable excipient:

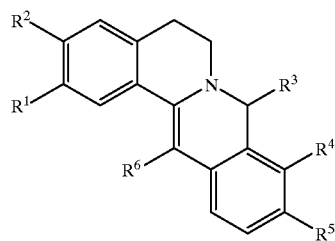

(1b)

wherein $R^1$ and $R^2$, which may be the same or different from each other, represent a hydroxy group or an alkoxy group having 1 to 4 carbon atoms or both of $R^1$ and $R^2$ represent a methylenedioxy group;

$R^3$ represents a hydrogen atom, an alkyl group having 1 to 8 carbon atoms, a ketonyl group having 3 to 7 carbon atoms, a cycloalkyl group having 3 to 7 carbon atoms, a cyanomethyl group, a 2-cyclopentanonyl group, or a 2-cyclohexanonyl group;

$R^4$ and $R^5$, which may be the same or different from each other, represent a hydroxy group, a hydroxyethylamino group or an alkoxy group having 1 to 4 carbon atoms;

$R^6$ represents a hydrogen atom, a branched alkyl group having 4 to 8 carbon atoms, a cyclic alkyl group having 3 to 8 carbon atoms, a straight chain alkyl group having 8 carbon atoms, an alkenyl group having 3 to 8 carbon atoms, or a cycloalkylakyl group having 3 to 7 carbon atoms.

8. The pharmaceutical composition according to claim 7, wherein the compound of formula (1b) or the pharmaceutically acceptable salt thereof is a sterol 14-reductase inhibitor.

9. A method for inhibiting cholesterol biosynthesis or treating hypercholesterolaemia or hyperlipidaemia in a patient, comprising:

administering to the patient an effective dose of a pharmaceutical composition comprising:
(a) an extract of *Corydalis Turtschaninowii Besser*, including a compound of chemical formula (1a) or a pharmaceutically acceptable salt thereof

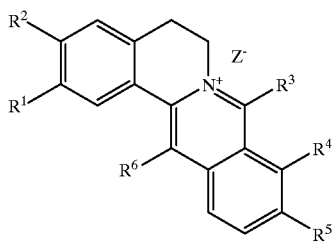

(1a)

wherein $R^1$ and $R^2$, which may be the same or different from each other, represent a hydroxy group or an alkoxy group having 1 to 4 carbon atoms or both of $R^1$ and $R^2$ represent a methylenedioxy group;

$R^3$ represents a hydrogen atom;

$R^4$ and $R^5$, which may be the same or different from each other, represent a hydroxy group, a hydroxyethylamino group or an alkoxy group having 1 to 4 carbon atoms;

$R^6$ represents a hydrogen atom, a branched alkyl group having 4 to 8 carbon atoms, a cyclic alkyl group having 3 to 8 carbon atoms, or a straight chain alkyl group having 8 carbon atoms, an alkenyl group having 3 to 8 carbon atoms, a cycloalkylalkyl group having 3 to 7 carbon atoms, a haloalkyl group having 1 to 4 carbon atoms, an ethoxycarbonyl group, an ethoxycarbonylmethyl group, a hydroxycarbonylmethyl group, a 1-ethoxycarbonylethyl group, or a 2-valerolactonyl group;

Z represents a halogen atom; and (b) a pharmaceutically acceptable exipient or carrier.

10. The method of claim 9, wherein the extract comprises 7, 18,13,13α-tetrahydrocoridaline.

11. The method of claim 9, wherein the extract is a sterol 14-reductase inhibitor.

* * * * *